(12) United States Patent
Lai et al.

(10) Patent No.: US 6,503,716 B1
(45) Date of Patent: Jan. 7, 2003

(54) COMPOSITIONS AND METHODS FOR EXTRACTING A NUCLEIC ACID

(75) Inventors: Lucy Tung-Yi Lai, Fremont, CA (US); Michael Shiu-Yan Ho, Fremont, CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/724,766

(22) Filed: Nov. 28, 2000

(51) Int. Cl.$^7$ .......................... C12Q 1/68; C07H 21/02; C07H 21/04
(52) U.S. Cl. .......................... 435/6; 536/23.1
(58) Field of Search .............................. 435/6; 536/23.1

(56) References Cited

U.S. PATENT DOCUMENTS

| | | |
|---|---|---|
| 3,879,216 A | 4/1975 | Austin |
| 4,421,680 A | 12/1983 | Shivar |
| 4,483,920 A | 11/1984 | Gillespie et al. |
| 4,844,745 A | 7/1989 | Nash et al. |
| 4,921,629 A | 5/1990 | Malihi et al. |
| 5,096,610 A | 3/1992 | Bingham |
| 5,158,710 A | 10/1992 | Van Eenam |
| 5,202,049 A | 4/1993 | Bingham |
| 5,227,276 A | 7/1993 | Roeschert et al. |
| 5,234,809 A | 8/1993 | Boom et al. |
| 5,340,682 A | 8/1994 | Pawlowski et al. |
| 5,444,094 A | 8/1995 | Malik et al. |
| 5,482,834 A | 1/1996 | Gillespie |
| 5,534,181 A | 7/1996 | Henkel et al. |
| 5,637,152 A | 6/1997 | Robinson et al. |
| 5,770,548 A | 6/1998 | Leskowicz et al. |
| 5,786,319 A | 7/1998 | Pederson et al. |
| 5,849,681 A | 12/1998 | Neumiller et al. |
| 5,888,308 A | 3/1999 | Sachdev et al. |
| 5,906,215 A | 5/1999 | Conroy |
| 5,965,512 A | 10/1999 | Smyth et al. |

FOREIGN PATENT DOCUMENTS

| | | |
|---|---|---|
| EP | 0 379 093 A1 | 7/1990 |
| EP | 0 405 986 A2 | 1/1991 |
| EP | 0 572 907 A2 * | 12/1993 |
| JP | 58009793 | 1/1983 |
| WO | WO 87/06621 | 11/1987 |
| WO | WO 97/09412 | 3/1997 |

OTHER PUBLICATIONS

Cox and Smulian, 1983, "A single–step procedure for the isolation of individual mRNA species from crude lysates of *Physarum polycephalum*," *FEBS Letters* 155(1): 73–80.

Krawetz et al., 1986, "Isolation and fractionation of total nucleic acids from tissues and cells,"*Journal of Biochemical and Biophysical Methods* 12:29–36.

Rathke et al., 1997, "Stability of dilute colloidal silica suspensions in the vicinity of the binodal curve of the system 2–bytoxyethanol/water,"*Journal of Colloid and Interface Science* 192:334–337.

* cited by examiner

Primary Examiner—Kenneth R. Horlick
Assistant Examiner—Teresa Strzelecka
(74) Attorney, Agent, or Firm—Pennie & Edmonds LLP

(57) ABSTRACT

The present invention provides aqueous compositions comprising sodium metasilicate and an ether and methods of using the compositions to extract a nucleic acid from a cell, virus or other source. The extracted nucleic acids can be used for a variety of purposes, including as a source of template DNA for a polymerase chain reaction.

27 Claims, 8 Drawing Sheets

US 6,503,716 B1

COMPOSITIONS AND METHODS FOR EXTRACTING A NUCLEIC ACID

FIELD OF THE INVENTION

This invention relates in general to methods, compositions and kits for rapidly and efficiently purifying nucleic acids from a biological sample.

BACKGROUND

Many of the techniques of modem molecular biology and molecular medicine begin with the isolation of a nucleic acid from a biological source. Typically, the nucleic acid is extracted from a cell or virus and then modified or manipulated with one or more enzymes. In order to be useful, the extraction process must meet at least three criteria. First, it must make the nucleic acid available for manipulation by the operator by removing it from the cell or virus that contains it. Second, it must remove inhibitors of enzymes what would otherwise interfere with the manipulation. Third, it must remove nucleases that would otherwise destroy the nucleic acid. Each of these criteria is especially difficult to satisfy when the source of the nucleic acid is not a relatively pure culture of cells or viruses, but instead contains other contaminants. These problems are especially great when the source of the nucleic acid is itself a minor component of the starting material. Such is the case, for example, when a nucleic acid is extracted from a food pathogen that is part of a food sample.

Most methods of DNA extraction comprise at least two steps. In the first step, the cell or virus is lysed by chemical treatment, boiling, enzymatic digestion of the cell wall, or mechanical forces. Lysis releases the DNA from the cell or virus and makes it available for manipulation. Centrifugation or filtration separates cell or viral debris from a crude fraction comprising the DNA and impurities such as inhibitors of enzymes and nucleases. In the second step, the DNA is purified by removing the inhibitors, nucleases and other unwanted proteins from the crude fraction. Traditionally, this has been accomplished by extracting the crude fraction with phenol and precipitating the DNA with ethanol or isopropanol. The phenol extraction removes protein contaminants. Unfortunately, phenol is a highly toxic and corrosive chemical, requiring the operator to wear protective clothing, gloves and safety glasses and to use a chemical hood. Before it can be used to extract DNA, the phenol must be equilibrated to a pH of greater than 7.8. The equilibration process is time consuming and dangerous, as it requires the phenol to be heated to 68° C. The phenol extraction step is made more efficient by combining the equilibrated phenol with chloroform and isoamyl alcohol in a ratio of 25:24:1. However, the mixture is stable at 4° C. for no more than a month, and chloroform is highly toxic and a suspected carcinogen. The alcohol precipitation is necessary to remove contaminants, including traces of phenol and chloroform. As a single phenol extraction or ethanol precipitation is typically not completely effective at removing impurities from the DNA, they often must be repeated several times in order to obtain DNA of acceptable purity. However, with each extraction and precipitation, a portion of the DNA is lost, resulting in lower yields. Each precipitation step also requires a drying step to remove all traces of alcohol from the DNA. The alcohol can be evaporated at ambient temperature and pressure, which is time consuming, or at elevated temperature and reduced pressure in a heated, vacuum-sealed centrifuge, which is not as slow but requires an expensive and complicated apparatus and a significant amount of operator time.

More recently, alternatives to the traditional method of DNA isolation have been developed that do not use phenol or chloroform. These alternative methods typically involve removing inhibitors, nucleases and other proteins by binding the DNA to a solid substrate such as a column, resin, filter or slurry. The DNA is washed one or more times to remove impurities, then eluted from the substrate. While these alternatives offer some advantages over the traditional methods, the binding substrates required are expensive and cannot be reused. Moreover, these methods require the operator to invest significant time and energy. Also, substrate-bound DNA can be susceptible to destruction by shearing.

The isolation of RNA presents even greater difficulties. Trace amounts of RNAse present during isolation can quickly destroy all of the RNA in a sample. The operator must both inactivate the RNAse that is originally present in the sample and prevent RNAse from outside sources being introduced into the sample. This is a difficult task because RNAses are ubiquitous, abundant and hardy enzymes. Most methods of isolating RNA are complicated and involve many time consuming steps, each step being an opportunity for the contamination of the sample with an RNAse that will destroy the desired RNA.

The shortcomings of the nucleic acid extraction methods described above are greatly multiplied when the starting material is not a relatively pure laboratory-grown culture, but instead is a crude sample. Examples of crude samples that have thwarted existing methods of nucleic acid isolation include food samples, clinical samples, forensic samples, agricultural samples and environmental samples. Making matters worse, the cell or virus that is the source of the nucleic acid often is a tiny fraction of the total mass of the sample. The nucleic acid must be separated from both the cell or viral debris and from the other material in the sample, and from any nucleases or inhibitors of enzymes that it contains. The problem is particularly acute when the nucleic acid is RNA, because RNAs are acutely sensitive to RNAse-catalyzed hydrolyis, or DNA that is to be amplified using the Polymerase Chain Reaction ("PCR") or another amplification technique. PCR requires only minute amounts of substrate DNA, but the polymerase enzyme used to amplify the DNA is sensitive to even trace amounts of inhibitors.

Accordingly, there is a need in the art for fast and efficient methods for isolating nucleic acids from biological samples. The present invention meets this need. The methods of the invention allow total nucleic acid to be isolated from virtually any biological source. The methods of the invention are especially useful under conditions where previous methods are ineffective or impractical: the biological sample contains large amounts of contaminating material, the source of the nucleic acid is a small fraction of the total biological sample, the isolation is large-scale or automated, or electricity or laboratory equipment are not available.

SUMMARY OF THE INVENTION

In one aspect, the present invention provides a simple, fast and efficient method for isolating nucleic acids from samples, typically from biological samples. According to the method, a biological sample is contacted with a nucleic acid extraction reagent for a period of time and at a temperature sufficient to lyse cells in the biological sample. Following lysis, the nucleic acids are recovered from the cell debris, typically by centrifuging the sample to pellet the cell debris and recovering the supernatant, which comprises the nucleic acids.

Nucleic acid extraction reagents useful in the methods of the invention are typically aqueous compositions comprising about 0.1% (w/w) to about 18% (w/w) sodium metasilicate and about 0.05% (w/w) to about 80% (w/w), and preferably about 0.5% (w/w) to about 40% (w/w) of a substituted ether. The weight ratio of the metasilicate to substituted ether is typically in the range of about 1:0.5 to about 1:2. In a preferred embodiment, the weight ratio of sodium metasilicate to substituted ether is about 1:1.3. Typical substituted ethers include, but are not limited to, alkoxy alkyl alcohols, aryloxy alkyl alcohols and alkyloxy aryl alcohols comprising from 2 to 12 carbon atoms, more typically from 3 or 4 to 8 carbon atoms. Preferred substituted ethers are unbranched primary alkoxy alkanols according to the formula $CH_3(CH_2)_m$—O—$(CH_2)_nCH_2OH$, where m and n are each, independently of one another, integers between 0 and 6. Examples of preferred alkylated alkyl alcohols include 2-butoxyethanol and 2-methoxyethanol. Additional substituted ethers include 2-phenoxyethanol, diethylene glycol-monobutyl ether, diethylene glycol-monoethyl ether, diethylene glycol-monopentyl ether, diethylene glycol-diethyl ether, diethylene glycol-dibutyl ether, ethylene glycol-monomethyl ether, ethylene glcyol-monoethyl ether, ethylene glcyol-monobutyl ether, ethylene glcyol-dimethyl ether and ethylene glcyol-diethyl ether.

The nucleic acid extraction reagents are typically basic, preferably having a pH in the range of about pH 7 to about pH 10, and may contain additional optional components, including but not limited to: organic acids such as citric acid or acetic acid, typically at a concentration in the range of about 0.0M to about 0.04M; buffering agents such as Tris-HCl, HEPES, MOPS, PIPES, MES typically at a concentration of about 10 mM to about 100 mM; chelating agents such as EDTA or EGTA, typically at a concentration in the range of about 0.1 mM to about 1 mM; resins such as cross-linked polystyrene beads (e.g., CHELEX™, Sigma-Aldrich, St. Louis, Mo.), cross-linked agarose beads with tris(2-aminoethyl)amine, iminodiacetic acid, Duolite C-467, Duolite GT73, typically at a concentration of 15% or less (w/w); preservatives such as $NaN_3$, typically at a concentration in the range of about 0.01% to about 0.4% (w/v); surfactants such as SDS, Triton X-100 or TWEEN, typically at a concentration in the range of about 0.1% to about 1.0% (w/v); and a stabilizer, such as polyethylene glycol, typically at a concentration in the range of about 0.03% (w/w) to about 1% (w/w). The intended use of the extracted nucleic acid can influence the concentration of each of the ingredients used in the extraction reagent. For example, when the extracted nucleic acid will be used in a PCR reaction, the extraction reagent should be formulated such that the concentration of ingredients in the PCR reaction will not inhibit Taq polymerase or otherwise prevent the amplification reaction from working. For factors influencing the success of PCR reactions, see Innis (ed.), 1995, PCR Strategies, Academic Press, especially Chapter 1.

The types of biological sources from which a nucleic acid may be isolated using the method of the invention are virtually limitless. For example, the nucleic acid may be isolated from a microorganism such as a bacterium (e.g., a eubacterium or an archaebacterium), virus, retrovirus, or eukaryote (e.g., yeast or other fungus). The microorganism can be a pathogenic microorganism. The nucleic acid also can be isolated from, for example, a plant or animal cell (e.g., a human cell). The cell or virus from which the nucleic acid is isolated can be part of virtually any type of sample. For example, the cell or virus can be part of a food, clinical, forensic, agricultural or environmental sample. These samples can comprise, for example, a bodily fluid (e.g., blood, semen, saliva), a tissue or other sample taken from a subject (e.g., a biopsy), dirt, water, or any other solid or liquid matter known to contain, or suspected of containing, a cell or virus.

In another aspect, the present invention provides nucleic acid extraction reagents specifically formulated for use in the method of the invention. Nucleic acid extraction reagents of the invention are typically aqueous compositions comprising from greater than 0.8% (w/w) to less than 5% (w/w) sodium metasilicate and from greater than 0.4% (w/w) to less than 5% (w/w) of a substituted ether.

In a preferred embodiment, the composition comprises between about 0.85% (w/w) to about 4% (w/w) sodium metasilicate. In a more preferred embodiment, the composition comprises between about 0.90% (w/w) and about 3% (w/w) sodium metasilicate. In a most preferred embodiment, the composition comprises between about 1% (w/w) and about 2% (w/w) sodium metasilicate.

In another preferred embodiment, the composition comprises between about 1.1% (w/w) and 4% (w/w) substituted ether. In a more preferred embodiment, the composition comprises between about 1.2% (w/w) and 3% (w/w) substituted ether. In a most preferred embodiment, the composition comprises between about 1.25% (w/w) and 2.5% (w/w) substituted ether.

In another preferred embodiment, the ratio of sodium metasilicate concentration to substituted ether concentration is between about 0.16:1 and about 5:1. In a more preferred embodiment, the ratio of sodium metasilicate concentration to substituted ether concentration is between about 0.5:1 and about 4:1. In a still more preferred embodiment, the ratio of sodium metasilicate concentration to substituted ether concentration is between about 0.7:1 and about 3:1. In a still more preferred embodiment, the ratio of sodium metasilicate concentration to substituted ether concentration is between about 0.8:1 and about 2:1. In a still more preferred embodiment, the ratio of sodium metasilicate concentration to substituted ether concentration is between about 0.9:1 and about 1:1.75. In a still more preferred embodiment, the ratio of sodium metasilicate concentration to substituted ether concentration is between about 1:1 and about 1:1.5. In a still more preferred embodiment, the ratio of sodium metasilicate concentration to substituted ether concentration is between about 1:1.2 and about 1:1.4. In a most preferred embodiment, the ratio of sodium metasilicate concentration to substituted ether concentration is about 1:1.3.

In another preferred embodiment, the composition has a pH in the range of about 7 or greater. In a more preferred embodiment, the composition has a pH in the range of about 7 to about 10.5. In a most preferred embodiment, the composition has a pH in the range of about 8 to about 9.5.

Typical substituted and preferred substituted ethers are those previously described. The nucleic acid extraction reagents also can contain additional optional components, described above.

In another aspect, the invention provides a kit comprising a nucleic acid extraction reagent useful for practicing the method of the invention. The kit may optionally include additional reagents, buffers and apparatuses for growing the samples from which the nucleic acids will be extracted and/or for carrying out subsequent analyses of the isolated nucleic acids, such as sequencing or PCR. For example, the kit may include a vessel for growing a sample or practicing the methods of the invention, a sequencing or PCR primer, a polymerase (e.g., a Taq polymerase) or other enzyme, a nucleotide triphosphate or mixture of nucleotide triphosphates, a microorganism, or medium for culturing a microorganism.

The nucleic acid extraction reagents and methods of the invention provide significant advantages over currently available isolation techniques. Quite importantly, nucleic acids isolated with the reagents and/or methods of the invention are substantially pure, and can be used directly in a variety of assays and/or analyses without further manipulation or purification. For example, nucleic acids isolated with the reagents and/or methods of the invention may be amplified, e.g. by PCR, or sequenced without further purification. The ability to efficiently isolate nucleic acids from a biological sample in a single step in high purity, especially in high enough purity for subsequent enzymatic manipulations such as PCR amplification, is unprecedented in the art.

DETAILED DESCRIPTION OF THE PREFERRED EMBODIMENTS

Figure 1A:
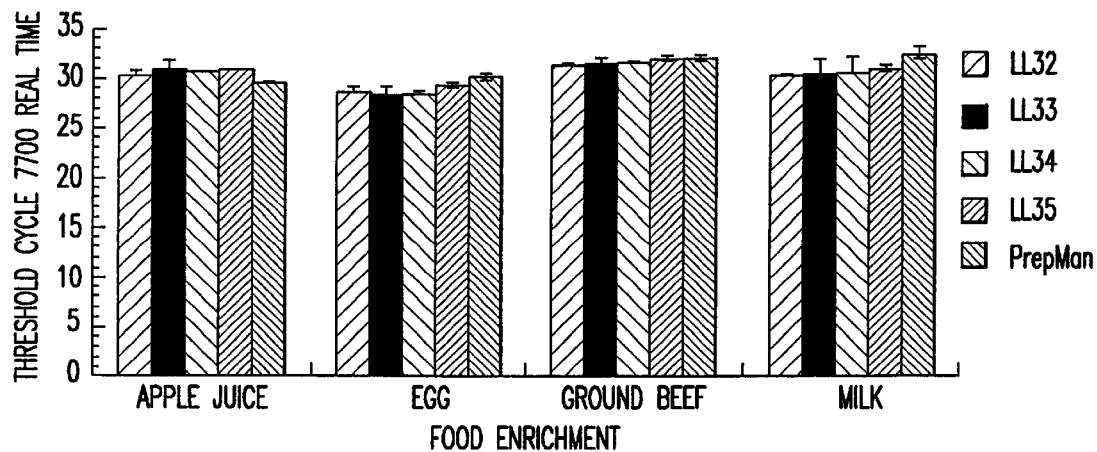
FIG. 1 shows the results of PCR amplification reactions using template DNA prepared using the methods and compositions of the instant invention as measured by threshold cycle (upper panel) and fluorescence intensity (lower panel).

The methods, compositions and kits of the present invention are useful for extracting nucleic acids from cells and viruses. They are extremely versatile and can be adapted for use in a large number and wide variety of applications, some of which are described in Sambrook et al. (ed.s), 1989, *Molecular Cloning: A Laboratory Manual*, Cold Spring Harbor Press, N.Y. and Ausubel et al. (ed.s), 2000, *Current Protocols in Molecular Biology*, John Wiley & Sons, N.Y. As will be described in more detail below, the compositions, methods and kits of the present invention can be used to isolate virtually any type of nucleic acid (e.g., any type of DNA or RNA) from virtually any type of cell (e.g., prokaryotic or eukaryotic), or from any type of virus (e.g., a DNA or RNA virus), in a sample derived from virtually any source (e.g., a cell culture, clinical sample, agricultural sample, environmental sample, forensic sample or food sample), under even primitive conditions (e.g., without electricity). The extracted nucleic acid can. be used, without further purification or washing, for virtually any purpose known in the art to which a nucleic acid extract can be put (e.g., an amplification reaction, sequencing reaction, labeling reaction, annealing reaction, restriction digest, ligation, reverse transcriptase reaction, hybridization, Southern blot or Northern blot). The compositions, methods and kits of the present invention are especially well-suited for preparing nucleic acid extracts for use in amplification techniques (e.g., PCR, LCR, MASBA, SDA and bDNA) and for use in any high throughput or automated process. The present invention also can be adapted to purify or wash a previously extracted nucleic acid. Furthermore, the compositions, methods and kits of the present invention are inexpensive, simple and quick to make or use compared to other nucleic acid extraction reagents, methods and kits known in the art. Unlike other methods of extracting nucleic acids, the methods of the invention can be performed without a heat source, centrifuge or vacuum desiccator. Thus, the methods of the invention are ideal for use in locations where electricity is not available. The nucleic acid extraction reagents also are environmentally safe.

According to the method of the invention, a sample containing or suspected of containing a nucleic acid of interest is contacted with a nucleic acid extraction reagent at a temperature and for a time sufficient to lyse cells in the sample, thereby releasing the nucleic acids into the extraction reagent. The released nucleic acids may then be isolated from the cell debris and other contaminants, typically by centrifuging the sample to pellet the cell debris and contaminants and separating the supernatant from the pellet. The isolated nucleic acids may then be used in further manipulations and arrays, such as, for example, PCR amplification reactions, without further purification.

Nucleic acid extraction reagents useful in the method of the invention are solutions comprising sodium metasilicate and a substituted ether. The reagents are typically neutral to basic, with a pH in the range of about pH 7 to about pH 10, and generally comprise from about 0.1% to about 18% (w/v) sodium metasilicate and about 0.05% to about 80% (v/v) substituted ether.

The identity of the substituted ether is not critical for success. Typical substituted ethers that can be used include, by way of example and not limitation, alkoxy alkyl alcohols, aryloxy alkyl alcohols and alkyloxy aryl alcohols comprising a total of from 2 to 12 carbon atoms; more preferably from three or four to eight carbon atoms. The alkyl groups may be straight-chain, branched or cyclic and may be saturated or unsaturated. The aryl groups are typically phenyl or naphthyl. Preferred substituted ethers are straight-chain primary alkoxy alkanols according to the formula $CH_3(CH_2)_m-O-(CH_2)_n CH_2OH$, where m and n, independently of one another, are integers between 0 and 6. Examples of preferred alkylated alkyl alcohols include 2-butoxyethanol and 2-methoxyethanol. Additional substituted ethers include 2-phenoxyethanol, diethylene glycol-monobutyl ether, diethylene glycol-monoethyl ether, diethylene glycol-monopentyl ether, diethylene glycol-diethyl ether, diethylene glycol-dibutyl ether, ethylene glycol-monomethyl ether, ethylene glcyol-monoethyl ether, ethylene glcyol-monobutyl ether, ethylene glcyol-dimethyl ether and ethylene glcyol-diethyl ether.

As will be appreciated by those of skill in the art, the nucleic acid extraction reagent may comprise mixtures of 2 or more substituted ethers. For example, the reagent may comprise a mixture of a primary alkoxy alkanol according to the above formula and an aryloxy alkyl alcohol. When mixtures of substituted ethers are used, the various amounts and ratios described herein refer to the total amount of substituted ether.

The nucleic acid extraction reagent may also comprise additional optional ingredients, including by way of example and not limitation, buffering agents, chelating agents, preservatives, etc. Any buffering agent suitable for maintaining the pH of the reagent in the range of pH 7 to pH 10 may be used, including for example, Tris-HCl, HEPES, MOPS, PIPES, MES, phosphate buffer, etc. The pH of the reagent may be adjusted with acid or base, for example HCl or NaOH. Alternatively, the pH may be adjusted with a weak acid or base, for example, with a weak organic acid such as citric acid or acetic acid. While not critical for success, the concentration of the buffering agent is typically in the range of 1 mM to 100 mM, more preferably in the range of 10 mM to 50 mM. success, the concentration of the buffering agent is typically in the range of 1 mM to 100 mM, more preferably in the range of 10 mM to 50 mM.

As will be discussed in more detail below, it is often times preferable to acidify the nucleic extraction reagent during preparation. Thus, the nucleic acid extraction reagent may further include an acid. Preferred acids are weak organic acids such as citric acid or acetic acid. When used, the final concentration of the organic acid will typically be in the range of 0.001 M to 0.5 M, more typically in the range of 0.01 M to 0.25 M, and most preferably in the range of 0.05 M to 0.2 M.

Chelating agents that optionally may be used include, but are not limited to EDTA or EGTA, typically in the range of about 0.1 mM to about 100 mM, more preferably in the range of about 0.5 mM to about 50 mM, and most preferably in the range of about 1 mM to about 10 mM. Chelating resins also may be used, including, but not limited to, cross-linked polystyrene beads (e.g., CHELEX™), cross-linked agarose beads with tris(2-amintoethyl)amine, iminodiacetic acid, Duolite C-467, Duolite GT73, typically at a concentration in the range of about 0.01% (w/v) to about 1% (w/v), more preferably about 0.025% (w/v) to about 0.5% (w/v), most preferably 0.05% (w/v) to about 0.2% (w/v).

Preservatives, e.g., sodium azide, also may be used. When used, preservatives are typically used at a very low concentrations, in the range of about 0.1% to 0.4%.

Stabilizers, e.g., polyethylene glycol, also may be used. When used, stabilizers are typically used at concentrations in the range of about 0.04% (w/w) to about 1% (w/w).

Other optional ingredients that may be used in the nucleic acid extraction reagents will be apparent to those of skill in the art. For example, the reagents also can comprise ingredients useful in the further manipulation of the extracted nucleic acids. For example, the reagents can comprise one or more of Taq polymerase buffer, Taq polymerase, nucleotide triphosphates, and primers at concentrations that facilitate PCR amplification of the extracted nucleic acid.

A variety of compositions containing sodium metasilicate and a substituted ether that may be successfully used as nucleic acid extraction reagents (after adjusting the pH as necessary) using the methods of the instant invention are described in, for example, U.S. Pat. No. 5,965,512, U.S. Pat. No. 5,906,215, U.S. Pat. No. 5,888,308, U.S. Pat. No. 5,849,681, U.S. Pat. No. 5,786,319, U.S. Pat. No. 5,770,548, U.S. Pat. No. 5,637,152, U.S. Pat. No. 5,534,181, U.S. Pat. No. 5,444,094, U.S. Pat. No. 5,340,682, U.S. Pat. No. 5,227,276, U.S. Pat. No. 5,096,610, U.S. Pat. No. 5,202,049, U.S. Pat. No. 5,158,710, U.S. Pat. No. 4,921,629, U.S. Pat. No. 4,844,745, U.S. Pat. No. 4,421,680, U.S. Pat. No. 3,879,216, Japanese Pat. App. No. JP 58009793, European Pat. App. No. 0 379 093 A1, European Pat. App. No. 0 405 986 A2 and PCT Pat. App. No. 97/09412, the disclosures of which are incorporated herein by reference.

In a preferred embodiment of the invention, the nucleic acid extraction reagent comprises about 1% to about 2% (w/w) sodium metasilicate and about 1.25% to 2.5% (w/w) of a substituted ether, such as 2-butoxy ethanol, 2-methoxyethanol, 2-phenoxyethanol, diethylene monoethyl ether, diethylene glycol butyl ether and diethylene glycol dibutyl ether, and has a pH in the range of pH 8.3 to pH 8.9. Preferably, the weight-to-weight ratio of the sodium metasilicate to alkoxy alkyl alcohol is in the range of 1:1.1 to 1:1.5, more preferably 1:1.3. The preferred composition also includes citric acid or acetic acid in the range of about 0.05 M to about 0.2 M. The preferred composition may also include any of the above-listed optional ingredients in the previously indicated amounts.

The nucleic acid extraction reagents may be prepared according to conventional techniques, such as the techniques taught in the above-listed patents and references. In one convenient embodiment, the nucleic acid extraction reagent is prepared by first dissolving the sodium metasilicate in water and diluting this solution with the substituted ether. The aqueous sodium metasilicate-substituted ether solution is then further diluted with an aqueous solution of weak organic acid. Finally, the resultant solution is diluted with buffer to achieve the desired pH.

It has been observed that sometimes a flocculent becomes suspended in the nucleic acid extraction reagent, either during preparation or subsequent storage. Once formed, the flocculent may be redissolved by gentle agitation and/or application of heat. However, the flocculent need not be redissolved. The presence of the flocculent does not adversely effect the ability of the reagent to extract nucleic acids when used in the methods of the invention. Thus, if a flocculent develops, the reagent may be used in the methods as is, or clarified according to the preference of the user. Details for preparing a variety of different nucleic acid extraction reagents according to the invention are provided in the Examples.

The temperature at which the nucleic acid extraction reagent is contacted with the sample is not critical for success. For example, the contacting may be carried out at ambient temperature, at temperatures above ambient temperature and at temperatures below ambient temperature. However, as it is believed that the temperature of the mixture affects the rate of cell lysis (discussed in more detail below), the choice of temperature will affect the time period during which the sample must contact the reagent. Generally, the rate of cell lysis increases with increasing temperatures. Thus, samples contacted at higher temperature can generally be contacted for less time with the same result. However, those of skill in the art will appreciate that nucleic acids are not infinitely stable at high temperatures. Thus, the temperature used should not be so high as to denature or otherwise degrade the nucleic acids to be extracted. Typically, temperatures ranging from ambient (approx. 25° C.) to about 120° C., more typically from about 55° C. to about 100° C. yield good results, although, as indicated above, the method works with temperatures below ambient temperature. The mixture can be heated during the contact step using any method or apparatus known in the art, for example, a heated water bath, a heating block, or a thermocycler. The operator also can reduce the rate of lysis by cooling the mixture, for example, by incubating the mixture in an ice bath or in a refrigeration unit.

In addition to temperature, other factors that affect the period of time during which the sample is contacted with the nucleic acid extraction reagent include, for example, the amount of nucleic acid desired to be extracted, the number or concentration of cells or viruses in the starting sample, the type of cell or virus being lysed and the subsequent use to which the nucleic acid will be put. One of skill in the art also will appreciate that the time period of the contacting step can be extended beyond the minimum necessary for lysis, and that the limiting factor will be the rate of degradation of the nucleic acid in the lysate. For example, the lysate can be left at ambient temperature for at least several days without degradation of the nucleic acids. By cooling the mixture to 4° C., the contacting step can be extended to nine months or longer. The mixture can be frozen for even longer storage.

For most samples, it has been found that a contact time of about 10 minutes gives satisfactory results for temperatures between 25° C. and 100° C.

Once the cells have been lysed via the contacting step, the released nucleic acids may be recovered from the cell debris and other particulate material using standard methods. Conveniently, the lysate can be separated into an aqueous phase, which comprises the released nucleic acids, and a solid phase. The separation can be accomplished by force of gravity, either by allowing the lysate to sit substantially undisturbed or via centrifugation.

Alternatively, cell and other debris may be removed by filtration. As nucleic acids often stick nonspecifically to certain materials such as glass, etc., a filter material that does not significantly bind nucleic acids nonspecifically should be selected.

A significant advantage of the method of the invention is that the isolated nucleic acids may be used directly in further assays and experiments without further purification. For example, as demonstrated in Example 2, the recovered supernatant may be run directly on an agarose gel for direct analysis of the isolated nucleic acids. As demonstrated in Examples 2–13, DNA from a variety of different samples, including foodstuffs and blood, isolated according to the method of the invention was used directly in PCR amplification experiments. According to those examples, the supernatant fraction was used directly as a source of template DNA for the PCR reaction. The supernatant fraction could also be used as a source of template DNA or RNA for other applications, such as sequencing, labeling reactions, or generating cDNA.

In its broadest sense, the method of the invention extracts all nucleic acids from all sources within the sample. If the operator wishes to separate a particular nucleic acid from the others, one or more additional steps can be added. For example, the isolated nucleic acids can be run on an agarose or polyacrylamide gel to separate the nucleic acids by size or topology. RNA or DNA can be removed by contacting the isolated nucleic acids with, respectively, RNAse or DNAse. Alternatively, the nucleic acid extraction reagent may include an RNAse or DNAse as desired, provided that the contacting step is performed at a temperature that does not denature or otherwise deleteriously affect the activity of the enzyme. A hybridization step can be added to separate nucleic acids according to their sequences. All of these various additional steps are conventional and will be apparent to those of skill in the art.

The methods of the present invention can be used to isolate virtually any type of nucleic acid, regardless of its length or sequence, from a cell, virus or other source. The operator need not know the sequence of the nucleic acid to be extracted. The nucleic acid can comprise non-traditional nucleotides, chemically modified nucleotides, artificial nucleotides or nucleotide substitutes. The nucleic acid also can comprise a non-nucleic acid component. For example, the nucleic acid can be covalently modified (e.g., with biotin) or otherwise labeled (e.g., with a radioactive isotope or fluorescent marker).

The nucleic acid can be, for example, a DNA or a RNA. The DNA molecule can be, for example, genomic DNA. Genomic DNA can be isolated using the methods of the invention from any source. It can be an entire chromosome or any part of a chromosome. It can be mutant or wild-type. It can comprise DNA from another source (e.g., a gene from another organism) introduced into the genomic DNA by any technique known in the art. It can comprise a coding sequence or a non-coding sequence. The coding sequence can encode, for example, a mRNA, a tRNA or an rRNA. The coding sequence can be wild-type or mutant, full-length or truncated. The non-coding sequence can be, for example, a centromere, a telomere, an intergenic region, an intron, a transposon, or a microsatellite sequence.

The DNA molecule also can be a plasmid DNA molecule. The plasmid DNA can be from any source or organism. The term "plasmid DNA" refers to all DNA molecules within a cell that are not part of the cell's normal complement of chromosomes. Thus, the term "plasmid" includes artificial chromosomes, extrachromosomal DNA and organellar DNA. The plasmid can be integrated into a host cell's chromosome or maintained as a circular or linear extrachromosomal element. It can be a naturally occurring plasmid or a genetically engineered plasmid. A genetically engineered plasmid can be derived from a natural source, for example, from the chromosomal DNA of an organism, such as a human, yeast, bacterium or virus. It can be maintained at high or low copy number in the host cell. It can contain all of the elements needed for its own, autonomous, propagation in the host cell, or it can rely on one or more host-encoded factors. It can be a plasmid useful for gene therapy. The plasmid can comprise one or more genes encoding an mRNA, tRNA or rRNA.

The nucleic acid also can be a cDNA. A cDNA is a DNA molecule made by reverse transcription of an RNA template, or by replication of a cDNA.

The nucleic acid also can be a RNA. The RNA can be from any natural or artificial source. Examples of RNA molecules that can be extracted using the methods, reagents and kits of the invention include mRNA, tRNA and rRNA.

The source of the nucleic acid can be any cell or virus, or any other composition, housing or structure comprising a nucleic acid. The nucleic acid can be extracted from any kind of cell, including both prokaryotic and eukaryotic cells. Any type of prokaryotic cell can be used, including eubacteria and archaebacteria, and gram-positive and gram-negative bacteria. The prokaryote can be a pathogenic bacterium. Any type of eukaryotic cell can be used, including, for example, a eukaryotic microorganism or a cell from a multicellular organism. The eukaryotic cell can be, for example, a pathogenic eukaryotic microorganism, a blood cell or a tissue cell.

Alternatively, the nucleic acid can be extracted from any kind of virus. The virus can have a RNA or a DNA genome. It can infect prokaryotic or eukaryotic cells. It can be a virulent, attenuated or non-infectious virus. It can be naturally occurring, artificially modified or artificially created. The virus can be, for example, a Human Immunodeficiency Virus ("HIV") or a virus derived therefrom. The virus can be, for example, part of a viral culture substantially free of the virus's host cell, or it can be isolated directly from an infected cell or tissue sample.

The source of the nucleic acid can be part of a larger sample. For example, the sample can be a food sample, a clinical sample, a forensic sample, an agricultural sample or an environmental sample. As is used herein, a "food sample" is a sample comprising food, a "clinical sample" is a sample used to diagnose, treat, monitor or cure a disease or disorder in the subject or to determine the subject's genotype, a "forensic sample" is a sample used to investigate a crime or accident, an "agricultural sample" is a sample taken from a plant or animal raised or reared for an agricultural purpose, and an "environmental sample" is a sample taken to assess the environmental quality of the source of the sample. Typically the sample will not be a pure culture of the source of the nucleic acid, but will contain other substances as well. The methods of the invention are effective at separating the nucleic acid from these other substances.

The sample can contain, in addition to the source of the nucleic acid, virtually any liquid or solid. The solid can be water soluble or water insoluble. For example, the methods of the invention can be used to detect the presence of a food pathogen in a food sample. This can be done by extracting genomic DNA from the food sample using the methods of the invention and amplifying the DNA using primers specific for the pathogen.

Alternatively, the sample can contain any substance derived from an animal subject, for example, blood, cerebral spinal fluid, hair, fur, saliva, sputum, semen, urine, stool, mucous, skin, a benign or malignant tumor or growth, biopsied tissue or any other type of tissue sample used in diagnosing a disease or condition. The subject can be any kind of animal, for example, a human. Alternatively, the sample can contain any substance derived from a plant subject, for example, leaf, stem, stalk, pollen, root, branch, flower, seed, bulb, spore or other plant material.

The nucleic acid extracted from the sample can be that of the subject. It can be used, for example, to determine whether the subject has a disease or medical condition, or to determine the subject's genotype, or to determine whether a certain gene is being expressed in the subject's tissue in the sample. Alternatively, the extracted nucleic acid can be that of a pathogen or other organism in the sample. The pathogen or organism can be, for example, a bacterium, virus (e.g., HIV), worm, insect or fungus. The nucleic acid can then be amplified using primers specific for the pathogen or other organism to detect the presence of the pathogen or other organism in the sample. Thus, the methods of the invention are useful in a wide variety of medical, clinical, forensic and agricultural applications.

Alternatively, the sample can comprise, for example, soil, dirt, landfill, garbage or waste, plant or animal matter, water (including, e.g., fresh water, salt water or waste water) or a sample collected from a structure (e.g., a building) or a device (e.g., an air conditioner). The extracted nucleic acid can be diagnostic of the presence of a microorganism in the sample. The microorganism can be pathogenic or otherwise harmful to another species, for example, to humans. The presence of the microorganism in the sample can be used to diagnose, assess, monitor or remedy environmental damage to the source of the sample (e.g., a deficiency or imbalance of nutrients or the presence of a toxin).

Although the method of the invention has been exemplified in terms of isolating a nucleic acid from a biological or other sample comprising a cell or virus, those of skill in the art will appreciate that the methods and reagents may be used to isolate and/or purify nucleic acids from virtually any source. For example, the methods and reagents may be used to isolate nucleic acids from in vitro reactions, such as in vitro transcription or reverse transcription reactions. Typically, the ratio of extraction reagent to in vitro synthesis product will be about 1 to 9.

The invention also provides kits useful for, e.g., analyzing samples for a nucleic acid of interest. The kits of the invention comprise a nucleic acid extraction reagent and one or more other additional components useful for the analysis or array desired. For example, the kit may additionally include one or more reagents useful for amplifying a nucleic acid of interest, including but not limited to, one or more amplification primers, one or more dioxy nucleotide triphorphates (e.g., a mixture of dATP, dGTP, dCTP and/or dUTP or dTTP)one or more polymerizing enzymes (e.g., Tag DNA polymer), etc.

Alternatively, the kit may include one or more additional reagents useful for sequencing a nucleic acid of interest, e.g., one or more sequencing primers (labeled or unlabeled), one or more deoxynucleotide triphosphates (e.g., a mixture of dATP, dGTP, dCTP and dUTP or dTTP), one or more labeled or unlabeled terminators (e.g., ddATP, ddGTP, ddCTP and ddUTP or ddTTP) or one or more polymerizing enzymes (e.g., DNA polymerase).

In yet another embodiment, the kit may include one or more reagents useful for labeling an isolated nucleic acid, e.g., one or more labeled or unlabeled deoxynucleotide triphosphates (e.g., a mixture of dATP, dGTP, dCTP and dUTP or dTTP), one or more polymerizing enzymes (e.g., DNA polymerase) or one or more labeled or unlabeled primers.

In yet another embodiment, the kit may include one or more reagents useful for making or using a DNA microarray, or "gene chip."

All references cited within the body of the instant specification are hereby incorporated by reference in their entireties.

EXAMPLE 1

Preparation of Compositions for Extracting a Nucleic Acid

This example demonstrates that a wide variety of reagents can be used to practice the methods of the instant invention.

The general procedure for preparing nucleic acid extraction reagents according to the invention was as follows. Sodium metasilicate was dissolved in a first volume of water, then mixed with a substituted ether (2-butoxy ethanol, unless otherwise specified). A weak citric acid solution and/or a Tris solution were optionally added, to achieve the desired pH, and the resulting mixture was optionally diluted further with a second volume of water. Other ingredients, including CHELEX-100™, sodium azide, and polyethylene glycol were then optionally added. The amount of each ingredient in each formula is indicated in the following table.

|  | LL-1 | LL-2 | LL-3 | LL-4 |
|---|---|---|---|---|
| SMS(9 $H_2O$) | 0.4 | 4 | 4 | 4 |
| $H_2O$ (mL) | 15.1 | 151 | 182 | 182 |
| Citric acid (powdered in g; sol'n (1:4 w/v) in mL) | 0.2 ml | 2 ml | 1.43 g | 1.33 g |
| Glacial acetic acid (mL) |  |  |  |  |
| $H_2O$ (mL) |  |  |  |  |
| 2BE (mL) | 0.5 | 5 | 5 | 5 |
| 1M Tris-HCL (pH 7.0) (mL) | 2 | 20 | 20.4 | 20.4 |
| Chelex-100 (g) |  |  |  |  |
| 5% (w/v) sodium azide (mL) | 0.178 | 1.78 | 2.04 | 2.04 |
| PEG (g) |  |  |  |  |
| Final pH | 8.5 | 8.5 | 8.2 | 8.3 |

|  | LL-5 | LL-6 | LL-7 | LL-8 |
|---|---|---|---|---|
| SMS($9H_2O$) (g) | 4 | 4 | 4 | 4 |
| $H_2O$ (mL) | 182 | 182 | 182.2 | 182.2 |
| Citric acid (powdered in g; sol'n (1:4 w/v) in mL) | 1.22 g | 1.13 g | 1.027 g | 1 g |
| Glacial acetic acid (mL) |  |  |  |  |
| $H_2O$ (mL) |  |  |  |  |
| 2BE (mL) | 5 | 5 | 5 | 5 |
| 1M Tris-HCL (pH 7.0) (mL) | 20.4 | 20.4 | 20.4 | 20.4 |
| Chelex-100 (g) |  |  |  |  |
| 5% (w/v) sodium azide (mL) | 2.04 | 2.04 | 2.04 | 2.04 |
| PEG (g) |  |  |  |  |
| Final pH | 8.4 | 8.5 | 8.7 | 8.6 |

|  | LL-9 | LL-10 | LL-11 | LL-12 |
|---|---|---|---|---|
| SMS(9 $H_2O$) | 4 | 4 | 4 | 4 |
| $H_2O$ (mL) | 182.3 | 182.4 | 187.9 | 183.6 |
| Citric acid (powdered in g; sol'n (1:4 w/v) in mL) | 0.919 g | 0.812 g | 1 g | 1.027 g |
| Glacial acetic acid (mL) |  |  |  |  |
| $H_2O$ (mL) |  |  |  |  |
| 2BE (mL) | 5 | 5 | 5 | 5 |
| 1M Tris-HCL (pH 7.0) (mL) | 20.4 | 20.4 | 15 | 19 |
| Chelex-100 (g) |  |  |  |  |
| 5% (w/v) sodium azide (mL) | 2.04 | 2.04 | 2.04 | 2.04 |
| PEG (g) |  |  |  |  |
| Final pH | 8.7 | 8.9 | 8.8 | 8.7 |

|  | LL-13 | LL-14 | LL-15 | LL-16 |
|---|---|---|---|---|
| SMS($9H_2O$) (g) | 3.802 | 4.3 | 4 | 4 |
| $H_2O$ (mL) | 185 | 190 | 183.6 | 183.6 |
| Citric acid (powdered in g; sol'n (1:4 w/v) in mL) | 0.9 g | 2 g |  |  |
| Glacial acetic acid (mL) |  |  | 0.75 | 0.65 |
| $H_2O$ (mL) |  |  |  |  |
| 2BE (mL) | 5 | 5.4 | 5 | 5 |
| 1M Tris-HCL (pH 7.0) (mL) | 19 | 1 | 19 | 19 |
| Chelex-100 (g) |  |  |  |  |
| 5% (w/v) sodium azide (mL) | 2.04 | 2 | 2.04 | 2.04 |
| PEG (g) |  |  |  |  |
| Final pH | 8.7 | 8.5 | 8.8 | 9 |

|  | LL-17 | LL-18 | LL-19 | LL-20 |
|---|---|---|---|---|
| SMS(9 $H_2O$) (g) | 4 | 4 | 3.8 | 3.8 |
| $H_2O$ (mL) | 183.6 | 183 | 100 | 100 |
| Citric acid (powdered in g; sol'n (1:4 w/v) in mL) |  |  | 0.9 g | 0.9 g |
| Glacial acetic acid (mL) | 0.85 | 1.1 |  |  |
| $H_2O$ (mL) |  |  | 84.3 | 85.25 |
| 2BE (mL) | 5 | 5 | 5.7 | 4.75 |
| 1M Tris-HCL (pH 7.0) (mL) | 19 | 19 | 19 | 19 |
| Chelex-100 (g) |  |  |  |  |
| 5% (w/v) sodium azide (mL) | 2.04 | 2.04 | 2.04 | 2.04 |
| PEG (g) |  |  |  |  |
| Final pH | 8.6 | 8.9 | 8.6 | 8.6 |

|  | LL-21 | LL-22 | LL-23 | LL-24 |
|---|---|---|---|---|
| SMS(9 $H_2O$) (g) | 3.8 | 3.8 | 1.27 | 1.27 |
| $H_2O$ (mL) | 100 | 100 | 33.33 | 33.33 |
| Citric acid (powdered in g; sol'n (1:4 w/v) in mL) | 0.9 g | 0.9 g | 0.30 g | 0.30 g |
| Glacial acetic acid (mL) |  |  |  |  |
| $H_2O$ (mL) | 86.2 | 88.1 | 28.33 | 28.33 |
| 2BE (mL) | 3.8 | 1.9 | 1.58 | 1.58 |
| 1M Tris-HCL (pH 7.0) (mL) | 19 | 19 | 6.33 | 6.33 |
| Chelex-100 (g) |  |  |  |  |
| 5% (w/v) sodium azide (mL) | 2.04 | 2.04 | 0.68 | 0.68 |
| PEG (g) |  |  | 0.07 | 0.21 |
| Final pH | 8.6 | 8.6 |  |  |

|  | LL-25 | LL-26 | LL-27 | LL-28 |
|---|---|---|---|---|
| SMS(9 $H_2O$) (g) | 1.27 | 3.5 | 3.5 | 3.5 |
| $H_2O$ (mL) | 33.33 | 100 | 100 | 100 |
| Citric acid (powdered in g; sol'n (1:4 w/v) in mL) | 0.30 g | 0.9 g | 0.829 g | 0.7 g |
| Glacial acetic acid (mL) |  |  |  |  |
| $H_2O$ (mL) | 28.33 | 85.75 | 89.4 | 89.4 |
| 2BE (mL) | 1.58 | 4.75 | 4.75 | 4.75 |
| 1M Tris-HCL (pH 7.0) (mL) | 6.33 | 19 | 17 | 20 |
| Chelex-100 (g) |  |  |  |  |
| 5% (w/v) sodium azide (mL) | 0.68 | 2.04 | 2.04 | 2.04 |
| PEG (g) | 0.70 |  |  |  |
| Final pH |  | 8.4 | 8.7 | 8.6 |

|  | LL-29 | LL-30 | LL-31 | LL-32 |
|---|---|---|---|---|
| SMS(9 $H_2O$) (g) | 2.1 | 2.1 | 3.5 | 2.1 |
| $H_2O$ (mL) | 100 | 100 | 100 | 100 |
| Citric acid (powdered in g; sol'n (1:4 w/v) in mL) | 0.5 g | 0.5 g | 0.83 g | 0.5 g |
| Glacial acetic acid (mL) |  |  |  |  |
| $H_2O$ (mL) | 89.4 | 95.4 | 88 | 97.5 |
| 2BE (mL) | 4.75 | 4.75 | 4.75 | 2.64 |
| 1M Tris-HCL (pH 7.0) (mL) | 17 | 10 | 19 | 10 |
| Chelex-100 (g) |  |  |  |  |
| 5% (w/v) sodium azide (mL) | 2.04 | 2.04 | 2.04 |  |
| PEG (g) |  |  |  |  |
| Final pH | 8.1 | 8.6 | 8.5 | 8.6 |

|  | LL-33 | LL-34 | LL-35 | LL-36 |
|---|---|---|---|---|
| SMS(9 $H_2O$) (g) | 2.1 | 2.1 | 2.7 | 2.1 |
| $H_2O$ (mL) | 100 | 100 | 100 | 100 |
| Citric acid (powdered in g; sol'n (1:4 w/v) in mL) | 0.5 g | 0.5 g | 0.61 g | 0.5 g |

-continued

|  |  |  |  |  |
|---|---|---|---|---|
| in mL) |  |  |  |  |
| Glacial acetic acid (mL) |  |  |  |  |
| H₂O (mL) | 94 | 92.4 | 91.8 | 92.9 |
| 2BE (mL) | 2.64 | 4.75 | 3.66 | 3.7 |
| 1M Tris-HCL (pH 7.0) (mL) | 13.5 | 13.5 | 15.66 | 13.5 |
| Chelex-100 (g) |  |  |  |  |
| 5% (w/v) sodium azide (mL) |  |  |  |  |
| PEG (g) |  |  |  |  |
| Final pH | 8.3 | 8.3 | 8.5 | 8.4 |

|  | LL-37 | LL-38 | LL-39 (gel out) | LL-40 (gel out) |
|---|---|---|---|---|
| SMS(9 H₂O) (g) | 2.1 | 2.1 | 2.1 | 2.1 |
| H₂O (mL) | 100 | 100 | 100 | 100 |
| Citric acid (powdered in g; sol'n (1:4 w/v) in mL) | 0.5 g | 0.5 g | 0.5 g | 0.5 g |
| Glacial acetic acid (mL) |  |  |  |  |
| H₂O (mL) | 91.3 | 92.4 | 94 | 94 |
| 2BE (mL) | 4.2 | 2.64 | 2.64 | 2.64 |
| 1M Tris-HCL (pH 7.0) (mL) | 14.6 | 13.5 | 13.5 | 13.5 |
| Chelex-100 (g) |  |  |  |  |
| 5% (w/v) sodium azide (mL) |  |  |  |  |
| PEG (g) |  |  | 0.21 | 2.1 |
| Final pH | 8.3 | 8.3 |  |  |

|  | LL-50 | LL-51 | LL-52 | LL-53 | LL-54 |
|---|---|---|---|---|---|
| SMS (g) | 4.2 | 4.2 | 4.2 | 4.2 | 4.2 |
| H₂O (mL) | 200 | 200 | 200 | 200 | 200 |
| Citric acid (g) | 1 | 1 | 1 | 1 | 1 |
| H₂O (mL) | 188 | 188 | 188 | 188 | 188 |
| Substituted ether (mL) | 5.28 (2-methoxy-ethanol) | 5.28 (2-phenoxy-ethanol) | 5.28 (2BE) | 5.28 (diethylene glycol butyl ether) | 5.28 (diethylene glycol dibutyl ether) |
| 1M Tris-HCL (pH 7.0) (mL) | 27 | 27 | 27 | 27 | 27 |
| Final pH | 8.5 | 8.5 | 8.5 | 8.5 | 8.5 |

|  | 16-1 | 16-2 | 19 | 21 |
|---|---|---|---|---|
| SMS (9H₂O unless otherwise indicated) (g) | 0.4 | 0.8 | 0.4 (SMS-5H₂O) | 0.8 |
| H₂O (mL) | 9.1 | 17.7 | 9.1 | 17.7 |
| 2BE (mL) | 0.5 | 1 | 0.5 | 1 |
| Citric acid sol'n (1:4 w/v) (mL) | 0.2 | 0.5 | 0.2 | 0.5 |
| Glacial acetic acid (mL) |  |  |  |  |
| CHELEX-100 ™ (g) | 0.5 | 0.5 | 0.5 | 0.75 |
| H₂O (mL) | 1.7 | 1.7 | 1.7 | 1.45 |
| 1M Tris-HCL (pH 7.0) (mL) |  | 0.25 |  | 0.25 |
| 1M Tris-HCL (pH 8.0) (mL) |  |  |  |  |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.5 | 0.2 | 0.25 | 0.25 |
| Citric acid sol'n (1:4 w/v) (mL) |  |  | 0.035 |  |
| 5% (w/v) sodium azide (mL) |  |  |  |  |
| PEG (g) |  |  |  |  |

|  | 22 | 23 | 24 (No Amp) | 25 (No Amp) |
|---|---|---|---|---|
| SMS (9H₂O unless otherwise indicated) (g) | 0.8 | 1.6 | 1.6 | 1.6 |
| H₂O (mL) | 17.7 | 15.4 | 15.4 | 15.4 |
| 2BE (mL) | 1 | 2 | 2 | 2 |
| Citric acid sol'n (1:4 w/v) (mL) | 0.5 | 0.75 | 0.75 | 0.75 |
| Glacial acetic acid (mL) |  |  |  |  |
| CHELEX-100 ™ (g) | 1 | 0.5 | 1 | 0.75 |
| H₂O (mL) | 1.2 | 1.7 | 1.2 | 1.45 |
| 1M Tris-HCL (pH 7.0) (mL) | 0.25 | 0.25 | 0.25 | 0.25 |
| 1M Tris-HCL (pH 8.0) (mL) |  |  |  |  |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.25 | 0.5 | 0.5 | 0.5 |
| Citric acid sol'n (1:4 w/v) (mL) |  |  |  |  |
| 5% (w/v) sodium azide (mL) |  |  |  |  |
| PEG (g) |  |  |  |  |

|  | 26 (No Amp) | 31 | 34 | 35 |
|---|---|---|---|---|
| SMS (9H₂O unless otherwise indicated) (g) | 1.6 | 0.4 | 0.4 | 0.4 |
| H₂O (mL) | 15.4 | 9.1 | 9.1 | 9.1 |
| 2BE (mL) | 2 | 0.5 | 0.5 | 0.5 |
| Citric acid sol'n (1:4 w/v) (mL) | 0.75 | 0.2 | 0.1 | 0.3 |
| Glacial acetic acid (mL) |  |  |  |  |
| CHELEX-100 ™ (g) | 0.75 | 0.5 | 0.5 | 0.5 |
| H₂O (mL) | 1.45 | 1.7 | 1.7 | 1.7 |
| 1M Tris-HCL (pH 7.0) (mL) | 0.25 |  |  |  |
| 1M Tris-HCL (pH 8.0) (mL) |  |  |  |  |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.5 | 0.5 | 0.5 | 0.5 |
| Citric acid sol'n (1:4 w/v) (mL) |  |  |  |  |
| 5% (w/v) sodium azide (mL) |  |  |  |  |
| PEG (g) |  |  |  |  |

|  | 36 | 37 | 38 | 43 |
|---|---|---|---|---|
| SMS (9H₂O unless otherwise indicated) (g) | 0.4 | 0.098 | 0.098 | 0.4 |
| H₂O (mL) | 9.1 | 2.23 | 3.93 | 9.1 |
| 2BE (mL) | 0.5 | 0.123 | 0.123 | 0.5 |
| Citric acid sol'n (1:4 w/v) (mL) | 0.15 | 0.049 | 0.049 | 0.2 |
| Glacial acetic acid (mL) |  |  |  |  |
| CHELEX-100 ™ (g) | 0.5 | 0.5 | 0.5 | 0.5 |
| H₂O (mL) | 1.7 | 1.7 | 1.7 | 1.7 |
| 1M Tris-HCL (pH 7.0) (mL) |  |  |  |  |
| 1M Tris-HCL (pH 8.0) (mL) |  |  |  |  |
| 0.5M EDTA (mL) | 0.005 | 0.005 | 0.005 | 0.005 |
| SMS/2BE/acid sol'n, prepared as above (mL) | 2.5 |  |  | 2.5 |
| Tris-HCL (7.0)(mL) | 0.5 | 0.5 | 0.5 | 0.2 |
| Citric acid sol'n (1:4 w/v) (mL) |  |  |  |  |

-continued

| | 44 | 45 | 46 | 47 |
|---|---|---|---|---|
| SMS (9H$_2$O unless otherwise indicated) (g) | 0.4 | 0.4 | 0.4 | 0.4 |
| H$_2$O (mL) | 9.1 | 9.1 | 9.1 | 9.1 |
| 2BE (mL) | 0.5 | 0.5 | 0.5 | 0.5 |
| Citric acid sol'n (1:4 w/v) (mL) | 0.2 | 0.2 | 0.15 | 0.15 |
| Glacial acetic acid (mL) | | | | |
| CHELEX-100 ™ (g) | 0.5 | 0.5 | 0.5 | 0.5 |
| H$_2$O (mL) | 1.7 | 1.7 | 1.7 | 1.7 |
| 1M Tris-HCL (pH 7.0) (mL) | | | | |
| 1M Tris-HCL (pH 8.0) (mL) | | | | |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.5 | 0.8 | 0.2 | 0.5 |
| Citric acid sol'n (1:4 w/v) (mL) | | | | |
| 5% (w/v) sodium azide (mL) | | | | |
| PEG (g) | | | | |

| | 48 | 49 | 50 | 51 |
|---|---|---|---|---|
| SMS (9H$_2$O unless otherwise indicated) (g) | 0.4 | 0.8 | 0.8 | 0.8 |
| H$_2$O (mL) | 9.1 | 18.2 | 18.2 | 18.2 |
| 2BE (mL) | 0.5 | 1 | 1 | 1 |
| Citric acid sol'n (1:4 w/v) (mL) | 0.15 | 0.4 | 0.4 | 0.4 |
| Glacial acetic acid (mL) | | | | |
| CHELEX-100 ™ (g) | 0.5 | 0.5 | 0.5 | 0.5 |
| H$_2$O (mL) | 1.7 | 1.7 | 1.7 | 1.7 |
| 1M Tris-HCL (pH 7.0) (mL) | | | | |
| 1M Tris-HCL (pH 8.0) (mL) | | | | |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.8 | 0.3 | 0.4 | 0.5 |
| Citric acid sol'n (1:4 w/v) (mL) | | | | |
| 5% (w/v) sodium azide (mL) | | | | |
| PEG (g) | | | | |

| | 52 | 53 | 54 | 55 |
|---|---|---|---|---|
| SMS (9H$_2$O unless otherwise indicated) (g) | 0.8 | 8 | 1.6 | 1.6 |
| H$_2$O (mL) | 18.2 | 182 | 36.4 | 36.4 |
| 2BE (mL) | 1 | 10 | 2 | 2 |
| Citric acid sol'n (1:4 w/v) (mL) | 0.4 | 4 | 0.8 | 0.8 |
| Glacial acetic acid (mL) | | | | |
| CHELEX-100 ™ (g) | 0.5 | 25 | | 0.26 |
| H$_2$O (mL) | 1.7 | 85 | | 1.94 |
| 1M Tris-HCL (pH 7.0) (mL) | | | 2.2 | |
| 1M Tris-HCL (pH 8.0) (mL) | | | | |
| 0.5M EDTA (mL) | 0.005 | 0.25 | 0.005 | 0.005 |
| SMS/2BE/acid sol'n, prepared as above (mL) | 2.5 | 125 | 2.5 | 2.5 |
| Tris-HCL (7.0)(mL) | 0.5 | 25 | 0.5 | 0.5 |
| Citric acid sol'n (1:4 w/v) (mL) | | | | |
| 5% (w/v) sodium azide (mL) | 0.05 | 2.5 | 0.05 | 0.05 |
| PEG (g) | | | | |

| | 56 | 57 | 58 | 59 |
|---|---|---|---|---|
| SMS (9H$_2$O unless otherwise indicated) (g) | 1.6 | 1.6 | 1.6 | 1.6 |
| H$_2$O (mL) | 36.4 | 36.4 | 36.4 | 36.4 |
| 2BE (mL) | 2 | 2 | 2 | 2 |
| Citric acid sol'n (1:4 w/v) (mL) | 0.8 | 0.8 | 0.8 | 0.8 |
| Glacial acetic acid (mL) | | | | |
| CHELEX-100 ™ (g) | 0.39 | 0.5 | 0.66 | 0.79 |
| H$_2$O (mL) | 1.81 | 1.7 | 1.54 | 1.41 |
| 1M Tris-HCL (pH 7.0) (mL) | | | | |
| 1M Tris-HCL (pH 8.0) (mL) | | | | |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.5 | 0.5 | 0.5 | 0.5 |
| Citric acid sol'n (1:4 w/v) (mL) | | | | |
| 5% (w/v) sodium azide (mL) | 0.05 | 0.05 | 0.05 | 0.05 |
| PEG (g) | | | | |

| | 60 | 61 | 62 | 63 |
|---|---|---|---|---|
| SMS (9H$_2$O unless otherwise indicated) (g) | 8 | 8 | 8 | 8 |
| H$_2$O (mL) | 182 | 182 | 182 | 182 |
| 2BE (mL) | 10 | 10 | 10 | 10 |
| Citric acid sol'n (1:4 w/v) (mL) | 4 | 4 | 4 | 4 |
| Glacial acetic acid (mL) | | | | |
| CHELEX-100 ™ (g) | | 0.25 | 0.79 | 1.31 |
| H$_2$O (mL) | 11 | 10.74 | 10.21 | 9.69 |
| 1M Tris-HCL (pH 7.0) (mL) | | | | |
| 1M Tris-HCL (pH 8.0) (mL) | | | | |
| 0.5M EDTA (mL) | 0.025 | 0.025 | 0.025 | 0.025 |
| SMS/2BE/acid sol'n, prepared as above (mL) | 12.5 | 12.5 | 12.5 | 12.5 |
| Tris-HCL (7.0)(mL) | 2.5 | 2.5 | 2.5 | 2.5 |
| Citric acid sol'n (1:4 w/v) (mL) | | | | |
| 5% (w/v) sodium azide (mL) | 0.25 | 0.25 | 0.25 | 0.25 |
| PEG (g) | | | | |

| | 64 | 65 | 66 | 67 |
|---|---|---|---|---|
| SMS (9H$_2$O unless otherwise indicated) (g) | 8 | 8 | 8 | 8 |
| H$_2$O (mL) | 182 | 182 | 182 | 182 |
| 2BE (mL) | 10 | 10 | 10 | 10 |
| Citric acid sol'n (1:4 w/v) (mL) | 4 | 4 | 4 | 4 |
| Glacial acetic acid (mL) | | | | |
| CHELEX-100 ™ (g) | 1.84 | 2.36 | 2.6 | 3.28 |
| H$_2$O (mL) | 9.16 | 8.64 | 8.4 | 7.72 |
| 1M Tris-HCL (pH 7.0) | | | | |

-continued

|  | | | | |
|---|---|---|---|---|
| (mL) | | | | |
| 1M Tris-HCL (pH 8.0) (mL) | | | | |
| 0.5M EDTA (mL) | 0.025 | 0.025 | 0.025 | 0.025 |
| SMS/2BE/acid sol'n, prepared as above (mL) | 12.5 | 12.5 | 12.5 | 12.5 |
| Tris-HCL (7.0)(mL) | 2.5 | 2.5 | 2.5 | 2.5 |
| Citric acid sol'n (1:4 w/v) (mL) | | | | |
| 5% (w/v) sodium azide (mL) | 0.25 | 0.25 | 0.25 | 0.25 |
| PEG (g) | | | | |

|  | 71 | 72 | 73 (No Amp) | 74 |
|---|---|---|---|---|
| SMS (9H$_2$O unless otherwise indicated) (g) | 1.6 | 1.6 | 1.6 | 1.6 |
| H$_2$O (mL) | 36.4 | 36.4 | 38.4 | 38.4 |
| 2BE (mL) | 2 | 2 | | |
| Citric acid sol'n (1:4 w/v) (mL) | 0.8 | 0.8 | 0.8 | 0.8 |
| Glacial acetic acid (mL) | | | | |
| CHELEX-100 ™ (g) | 0.26 | 0.26 | | 0.26 |
| H$_2$O (mL) | 1.94 | 1.94 | 1.94 | 1.94 |
| 1M Tris-HCL (pH 7.0) (mL) | | | | |
| 1M Tris-HCL (pH 8.0) (mL) | | | | |
| 0.5M EDTA (mL) | 0.005 | 0.005 | 0.005 | 0.005 |
| SMS/2BE/acid sol'n, prepared as above (mL) | 2.5 | 2.5 | 2.5 | 2.5 |
| Tris-HCL (7.0)(mL) | 0.5 | 0.5 | 0.5 | 0.5 |
| Citric acid sol'n (1:4 w/v) (mL) | | | | |
| 5% (w/v) sodium azide (mL) | 0.05 | 0.05 | 0.05 | 0.05 |
| PEG (g) | 0.025 | 0.04 | 0.025 | 0.025 |

|  | 75 | 76 | 77 | 78 |
|---|---|---|---|---|
| SMS (9H$_2$O unless otherwise indicated) (g) | 1.6 | 1.6 | 1.6 | 4 |
| H$_2$O (mL) | 36.4 | 36.4 | 36.4 | 170.4 |
| 2BE (mL) | 2 | 2 | 2 | 5 |
| Citric acid sol'n (1:4 w/v) (mL) | | | | 1.21 |
| Glacial acetic acid (mL) | | | | |
| CHELEX-100 ™ (g) | 1.25 | 2.5 | 1.25 | 10.4 |
| H$_2$O (mL) | 11.25 | 10 | 11.25 | 11 |
| 1M Tris-HCL (pH 7.0) (mL) | | | | |
| 1M Tris-HCL (pH 8.0) (mL) | | | | |
| 0.5M EDTA (mL) | 0.025 | 0.025 | 0.025 | 0.204 |
| SMS/2BE/acid sol'n, prepared as above (mL) | 12.5 | 12.5 | 12.5 | |
| Tris-HCL (7.0)(mL) | 0.25 | 0.25 | 0.175 | 20.408 |
| Citric acid sol'n (1:4 w/v) (mL) | | | | |
| 5% (w/v) sodium azide (mL) | 0.25 | 0.25 | 0.25 | 2.041 |
| PEG (g) | | | | |

|  | 27 | 28 | 29 | 30 |
|---|---|---|---|---|
| SMS (g) | 0.4 | 0.4 | 0.4 | 0.4 |
| H$_2$O (mL) | 16.24 | 16.24 | 16.24 | 16.24 |
| 2BE (mL) | 0.5 | 0.5 | 0.5 | 0.5 |
| Citric acid (g) | 0.05 | 0.1 | 0.15 | 0.2 |
| 0.5M EDTA (mL) | 0.0204 | 0.0204 | 0.0204 | 0.0204 |
| CHELEX-100 ™ (g) | 2.04 | 2.04 | 2.04 | 2.04 |
| 1M Tris-HCl (7.0) (mL) | 2.04 | 2.04 | 2.04 | 2.04 |

SMS: Sodium metasilicate (nonahydrate unless otherwise specified), Sigma Chemical, St. Louis MO
H$_2$O: 18 Megohm water, Sigma Chemical, St. Louis MO
2BE: 2-butoxyethanol, Sigma Chemical, St. Louis MO
Citric acid: J. T. Baker, Phillipsburg NJ
Acetic acid: Sigma Chemical, St. Louis MO
CHELEX-100 ™: Bio-Rad Laboratories, Hercules CA
Tris-HCl: Sigma Chemical, St. Louis MO
EDTA: Sigma Chemical, St. Louis MO
Sodium azide: Sigma Chemical, St. Louis MO
PEG: Polyethylene glycol, Sigma Chemical, St. Louis MO Each reagent listed in the table (except those marked "gel out," which produced a gelatinous residue during or after preparation) was tested for its ability to extract bacterial DNA essentially free of PCR inhibitors from an egg sample post-spiked with *E. coli* strain O157:H7, essentailly as described in Example 2. Every tested reagent gave a positive result in the bacterial DNA amplification assay, except for those labeled "no amp."

EXAMPLE 2

Extraction and Amplification of Bacterial DNA Food Samples

This example demonstrates the versatility of the methods and compositions of the claimed invention in extracting bacterial DNA from food samples.

| Manufacturer | Food | Manufacturer | Food |
|---|---|---|---|
| GERBER | Baby Cereal Mix | SAFEWAY | Cole Slaw |
| — | Fresh rainbow trout | SAFEWAY | Potato Salad |
| SAFEWAY | Fresh shrimp | GOOSE POINT | Oysters |
| OSCAR MAYER | Beef frank | — | Fresh lettuce |
| KELLOGG'S | Corn Flakes | — | Fresh alfalfa sprouts |
| SCHILLING | Italian seasoning mix | ODWALLA | Orange juice |
| ODWALLA | Apple juice | LUCERNE | Whole milk |
| NESTLE CARNATION | Hot cocoa mix (rich chocolate) | PACE | Thick and chunky salsa (mid) |
| KRAFT | American cheese | HEINZ | Mayonnaise |
| SAFEWAY | Ground beef | HAAGEN-DAZ | Chocolate chip chocolate ice cream |
| — | Imitation crab meat | FOSTER FARM | Ground chicken |
| LUCERNE | Coffee and cream yoghurt | — | Fresh strawberries |
| NESTLE CARNATION | Non-dairy coffee creamer | NESTLE | Chocolate chip cookie dough |
| LUCERNE | Egg | NESTLE CARNATION | Goodstart baby formula concentrate |
| NEW YORK STYLE SAUSAGE CO. | Italian sausage (ground pork) | COLUMBUS | Italian dry salami |
| LAND O' LAKES | Butter | CAMPBELL | Chicken noodle soup (canned) |

Each food sample was tested essentially as described in the Food and Drug Administration's Bacteriological Analytical Manual, 1998, AOAC International, Gaithersburg, Md. In separate experiments, 5 mL of milk, baby formula, apple juice, orange juice or non-dairy creamer was added to 45 mL of modified EC broth in an enrichment bag. For each of the other foods, in separate experiments, 10 g was added to 90 mL of modified EC broth in an enrichment bag. Each food enrichment was homogenized by placing the bag in a STOMACHER-400™ Laboratory Blender (Seward, London, England) and mixing for 1 minute, then incubated at 37° C. for 20 hours. Three-0.9 ml aliquots of each homogenate were then post-spiked to a concentration of approximately $1.1 \times 10^4$ cfu/ml with an appropriately diluted overnight culture of E. coli strain O157:H7 in 2 ml microcentrifuge tubes. The tubes were centrifuged for 2 minutes at 16,000 g. The supernatant fraction was removed from each tube and discarded without disturbing the pellet. 200 µl of reagent 53 (described in Example 1, above) was added to each pellet, then incubated in a boiling water bath for 10 minutes. The tubes were then centrifuged for 5 minutes at 16,000 g. 70 µl of the supernatant fraction from each tube was pipetted into a clean tube. The TAQMAN™ E. coli O157:H7 Pathogen Detection Kit (Applied Biosystems, Foster City, Calif.) was used according to the manufacturer's instructions to determine whether bacterial DNA could be detected in the food samples using a PCR protocol. Thermocycling was performed and the resulting amplification assayed using an ABI PRISM 7700™ Sequence Detector (Applied Biosystems, Foster City, Calif.) according to the manufacturer's directions. Briefly, the amplification of bacterial DNA sequences was measured using a first fluorescent probe. Each amplification reaction also included an internal positive control comprising a control DNA sequence, primers, and a second fluorescent probe. The probes fluoresce at different wavelengths and so the fluorescence of each probe can be measured independently of the other. The success or failure of each reaction was determined by following changes in the amount of fluorescence for each probe. A positive result, indicating that bacterial DNA was amplified and detected in the sample, was defined as a reaction wherein the fluorescence of both probes increased significantly over background (as determined by the sequence detector's manufacturer-supplied software). A negative result was one wherein the bacterial sequence probe's fluorescence did not increase significantly but the internal control sequence probe's fluorescence did increase. This indicated the extracted food sample lacked bacterial DNA (this result was mimicked by a negative control reaction containing the positive control template DNA but not bacterial template DNA). A "no amplification" result was one wherein neither probe increased in fluorescence significantly. Thus, the extracted food sample contained either a PCR inhibitor or a substance that interfered with the measurement of the probes' fluorescence (this result was mimicked by a negative control reaction which lacked Taq polymerase).

Following the above protocol, positive results were obtained for every sample tested except the Italian seasoning mix, cocoa mix and chocolate ice cream. All three Italian seasoning mix samples and two of the three chocolate ice cream samples gave negative results. The remaining chocolate ice cream sample and all three cocoa mix samples gave "no amplification" results. It was noted that these three samples had a distinct coloration that may have interfered with the measurement of fluorescence in the samples. Thus it is possible that by adding an appropriate filtration step to the method described above positive results could be obtained from these foods as well, although this was not tested.

EXAMPLE 3

Figure 1B:
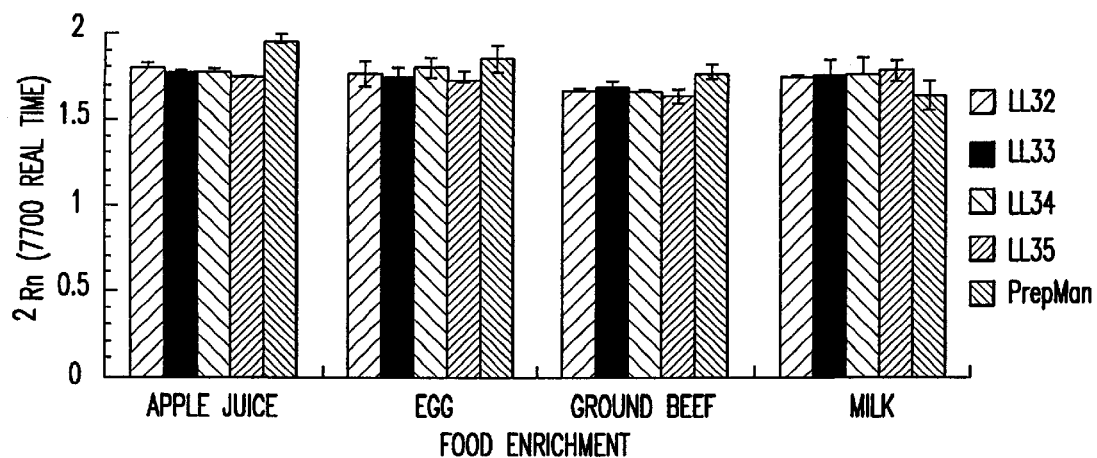

Extraction and Amplification of Bacterial DNA Using a Variety of Extraction Reagents Separate samples were prepared using either apple juice, egg, ground beef or milk. To prepare each sample, 25 g of the appropriate food was mixed with 225 ml of enrichment medium (e.g., modified EC broth) in a filter bag. Each bag was then incubated for 16–24 hours at 37° C. 0.9 ml of enrichment medium was removed from each bag and mixed with 0.1 ml of a dilution of an overnight culture of E. coli O157:H7 such that the final concentration of bacteria in the amplification reaction described below was 350 cfu/reaction. The 1 ml of post-spiked enrichment medium was centrifuged for 3 minutes in a microcentrifuge at maximum speed. The supernatant fraction was removed and discarded. Each pellet was resuspended in 200 µl of LL-32, LL-33, LL-34 or LL-35 (described in Example 1, above), or in PREPMAN™ Sample Preparation Reagent (Applied Biosystems, Foster City, Calif.) used according to the manufacturer's instructions, and incubated in a boiling water bath for 10 minutes. Each tube was allowed to cool at ambient temperature for 2 minutes, then centrifuged at maximum speed for 3 minutes in a microcentrifuge tube to pellet debris. 5 µl of each supernatant fraction was added to 45 µl of the TAQMAN™ E. coli O157:H7 PCR Detection System (Applied Biosystems, Foster City, Calif.) PCR mix and assayed on an ABI PRISM 7700™ Sequence Detection System (Applied Biosystems, Foster City, Calif.), essentially as described in Example 2. As shown in FIG. 1, all four reagents gave positive and virtually identical results for all four food samples tested. In the upper panel, the threshold cycle for each food sample extracted with each tested reagent is given. The threshold cycle is defined as the PCR amplification cycle at which the sequence detector detects amplification of the target bacterial sequence. Thus, the lower the threshold cycle, the more sensitive the detection. For each combination of food sample and extraction reagent tested, the threshold cycle was approximately 28 to 32. The lower panel depicts the amount of fluorescence measured by the detector at the completion of 40 rounds of amplification. This value ranged from between about 1.7 to about 1.9.

EXAMPLE 4

Extraction and Amplification of DNA from a Variety of Bacterial Sources

This example demonstrates that the compositions and methods of the invention can be used to extract and detect DNA from a wide variety of pathogenic bacteria in food samples.

Overnight food enrichments using egg and milk were prepared as described in Example 3. In separate experiments, 0.9 ml aliquots of each enrichment were post-spiked with 0.1 ml of a serial dilution of an overnight culture of either E. coli, Salmonella enteritidis or Listeria monocytogenes. Each post-spiked sample was centrifuged for 3 minutes in a microcentrifuge at maximum speed and the supernatant fraction discarded. Each cell pellet was resuspended in 200 µl of reagent LL-33 (described in Example 1, above), incubated for 10 minutes in a boiling water bath and centrifuged as before. Bacterial DNA also was extracted and amplified from serial dilutions of homogenous overnight cell cultures.

5 µl of each E. coli, S. enteritidis, and L. monocytogenes DNA extraction was amplified and detected using the TAQMAN™ STX1 Detection Assay (Applied Biosystems, Foster City, Calif.), TAQMAN™ Salmonella Gold Detection Assay (Applied Biosystems, Foster City, Calif.) and TAQMAN™ Listeria monocytogenes Detection Assay (Applied Biosystems, Foster City, Calif.), respectively, and an ABI PRISM 7700™ Sequence Detector (Applied Biosystems, Foster City, Calif.), all according to the manufacturer's instructions.

Figure 2:
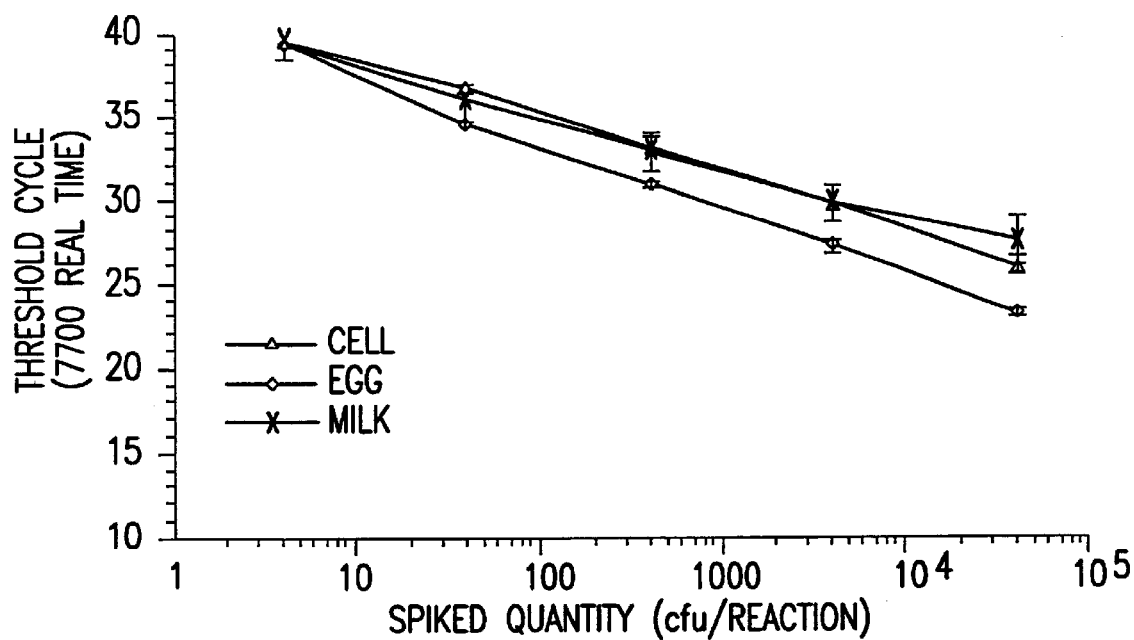
FIG. 2 shows the results of PCR amplification reactions using *E. coli* genomic DNA prepared using the methods and compositions of the instant invention as measured by threshold cycle.
Figure 3:
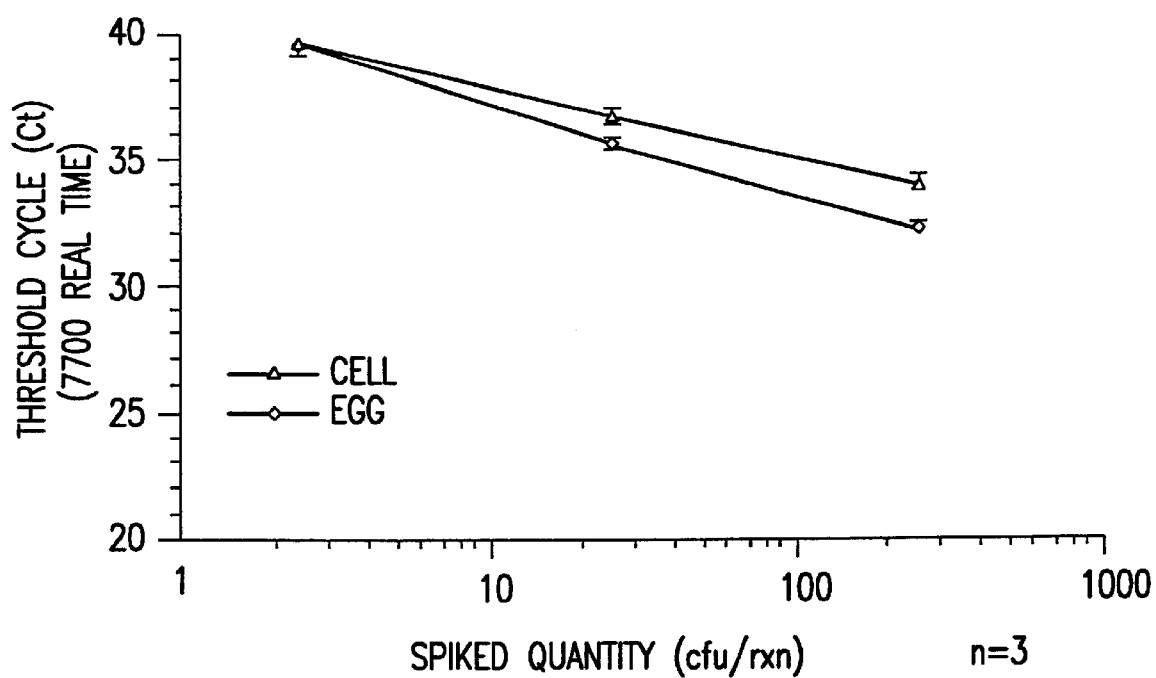
FIG. 3 shows the results of PCR amplification reactions using *Salmonella enteritidis* genomic DNA prepared using the methods and compositions of the instant invention as measured by threshold cycle.
Figure 4:
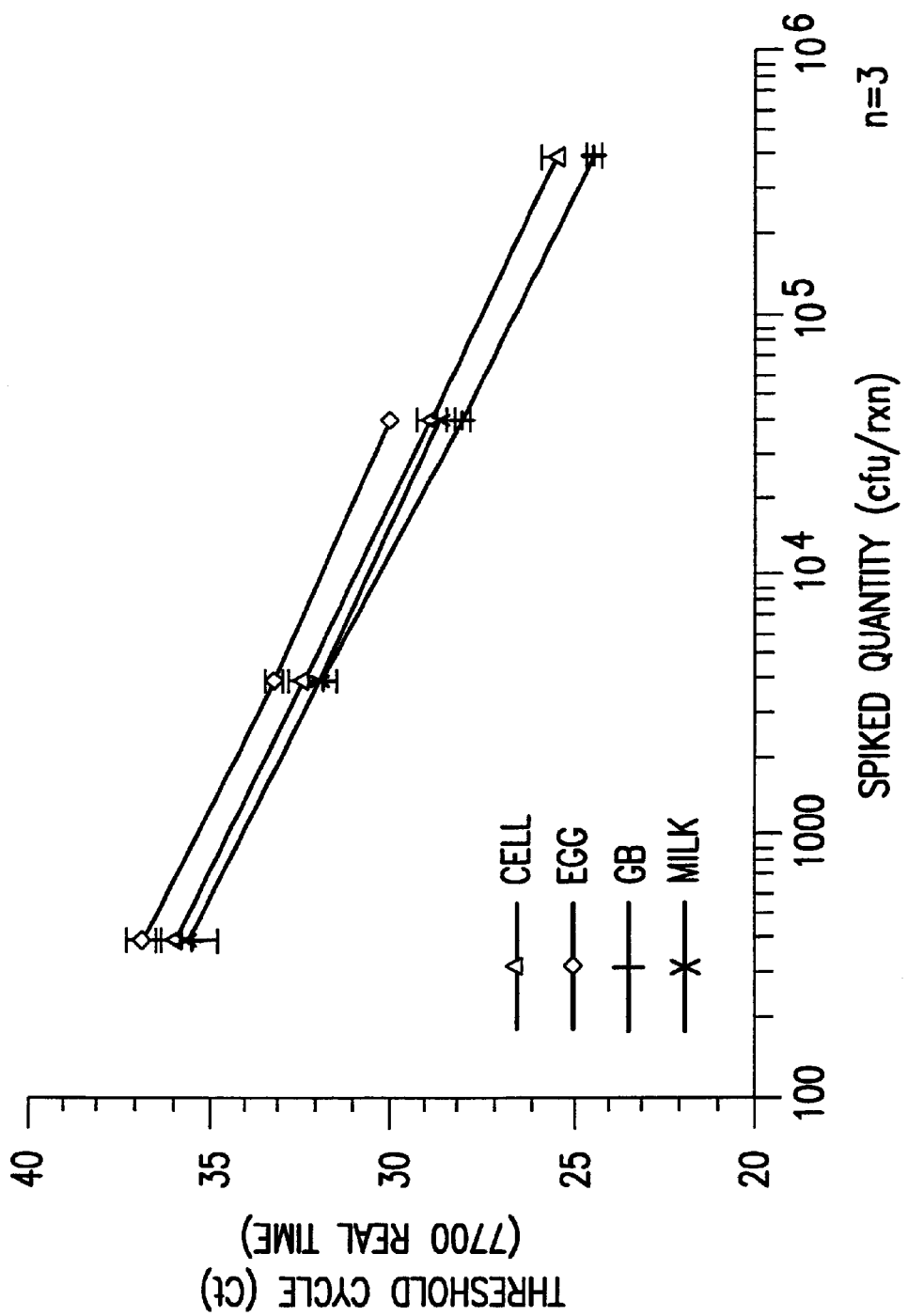
FIG. 4 shows the results of PCR amplification reactions using *Listeria monocytogenesi* genomic DNA prepared using the methods and compositions of the instant invention as measured by threshold cycle.

FIGS. 2, 3 and 4 show the threshold cycle for detecting *E. coli, S. enteritidis,* and *L. monocytogenes* DNA, respectively, from post-spiked food samples and from serial dilutions of overnight cell cultures. The concentration of bacteria is expressed as the number of colony forming units ("cfu") per amplification reaction.

EXAMPLE 5

Extraction and Visualization of Bacterial DNA and RNA

This example demonstrates that the methods and compositions of the instant invention can be used to isolate large amounts of DNA and RNA from a bacterial source, and that the nucleic acids in these extracts are stable at ambient temperature for over a week.

Figure 5A:
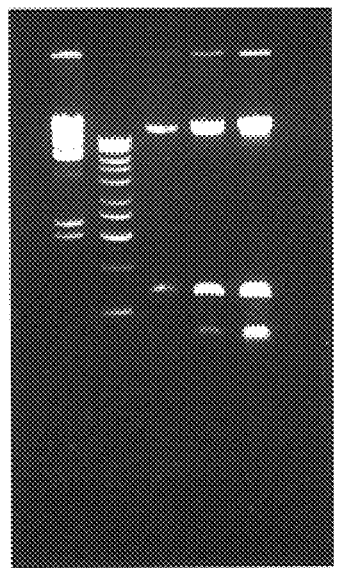
FIGS. 5A and 5B show electrophoretic separations on ethidium bromide-stained agarose gels of DNA extracted according to the method of the invention from *Listeria innocua*.

1 ml of tryptic soy broth was innoculated with *Listeria innocua* cells and incubated at 37° C. overnight with agitation. The standard plate count after 2 days was $9.5 \times 10^8$ cfu/ml. 400 µl of the culture was centrifuged at 16,000 g for 3 minutes. The supernatant fraction was removed and discarded. The cell pellet was resuspended in 200 µl of LL-12 (described in Example 1, above) by repeated pipetting. After a 10 minute incubation at ambient temperature, cell debris was removed by centrifuging at 16,000 g for 3 minutes. 1, 5 and 10 µl aliquots of the supernatant fraction were run alongside size markers on a 1% FMC SEAKEM™ agarose gel. The gel was stained with ethidium bromide. FIG. 5A. Lane 1: Hind III digest of lambda DNA (unheated); lane 2: 1 kB DNA ladder; lane 3: 1 µl *L. innocua* extract; lane 4: 5 µl *L. innocua* extract; lane 5: 10 µl *L. innocua* extract. A significant amount of *L. innocua chromosomal* DNA and rRNA was visible in each lane receiving an aliquot of the supernatant from the cell Lysis.

Figure 5B:
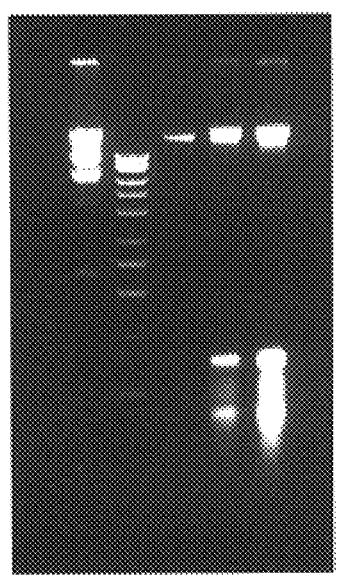

In order to determine the stability of the extracted DNA and RNA, the remaining portion of the supernatant fraction was left at ambient temperature for 10 days. 1, 5 and 10 µl aliquots were again run on a gel and stained as described above. FIG. 5B (same lane assignments as above). Although some degradation was visible, as evidenced by the smeared appearance of some of the bands, the DNA and RNA remained largely intact.

EXAMPLE 6

Detection of Genetically Modified Organisms in Soy-Containing Food Samples

This example demonstrates that the methods and compositions of the instant invention can be used to identify the presence of genetically modified organisms ("GMO") in a food sample.

All of the soy-containing food samples listed below were purchased at supermarkets. None was labeled as containing GMO. 100 mg of each food sample was suspended in 200 µl of reagent LL-33 (described in Example 1, above) in a microcentrifuge tube and incubated in a boiling water bath for ten minutes. 1 ml 1M TE (pH 7.0) was added to each suspension, which was then centrifuged at 16,000 g for 3 minutes. DNA also was extracted from a set of commercially available standards containing 0.1%, 0.5% and 2.0% GMO soy. 5 µl of each supernatant was removed and added to 20 µl of PCR mix. The PCR mix included primers complementary to a DNA sequence found in GMO soy but not in unmodified soy. Amplification and detection of the extracted DNAs was achieved essentially as described in Example 2 using an ABI PRISM 7700™ Sequence Detector (Applied Biosystems, Foster City, Calif.), which measured the threshold cycle ("Ct") for each sample. The threshold cycle is the time during amplification, measured by the number of amplification cycles performed, at which the sequence detector first detects an increase above background of the diagnostic fluorescence signal. The percentage of GMO contained in each sample was estimated by comparison of its Ct to the Ct of the GMO standards.

The following table lists soy-containing food products that were used in this example and their estimated GMO content.

| Food | % GMO | Food | % GMO |
|---|---|---|---|
| Baby Formula | >5% | Protein Bar #1 | >5% |
| Miso Soup Mix | >5% | Protein Bar #2 | 0.2% |
| Protein Drink | >5% | Protein Bar #3 | >5% |
| Soy Milk | >5% | Protein Bar #4 | >5% |
|  |  | Artificial Bacon Pieces | >5% |

EXAMPLE 7

Extraction and PCR of Bacterial DNA from Cheese

This example further demonstrates that the methods and compositions of the instant invention can be used to extract and amplify DNA from a variety of food samples.

In separate experiments, enriched cultures were prepared by mixing 10 g of American cheese, Boursin cheese, Cheddar cheese, Creme de Brie, Swiss cheese, egg, ground beef, milk or salad mix with 90 ml of modified EC broth in an enrichment bag and homogenized for 1 minute in a STOMACHER-400™ Laboratory Blender (Seward, London, England) as described in Example 2, above. The homogenates were then incubated at 37° C. for 23 hours. 0.9 ml aliquots of each sample were then post-spiked to a final concentration of $1.3 \times 10^5$ cfu/ml with an appropriately diluted overnight culture of *E. coli* O157:H7 in a screw top microcentrifuge tube and centrifuged for 3 minutes in a microcentrifuge at maximum speed. The supernatant fraction was removed and discarded. Each pellet was resuspended in 200 µl of reagent 60, 63 or 66 (described in Example 1, above) and incubated in a boiling water bath for 10 minutes. Each tube was allowed to cool at ambient temperature for 2 minutes, then centrifuged at maximum speed for 3 minutes in a microcentrifuge tube to pellet debris. 5 µl of each supernatant fraction was added to 45 µl of the TAQMAN™ *E. coli* STX PCR assay (Applied Biosystems, Foster City, Calif.) PCR mix and amplified and assayed on an ABI PRISM 7700™ Sequence Detection System (Applied Biosystems, Foster City, Calif.), essentially as described in Experiment 2.

Most food samples gave positive results with all three tested reagents. The only exception was cheddar cheese, which gave positive results with reagents 60 and 66 but not with reagent 63.

EXAMPLE 8

Extraction and Amplification of DNA from Human Blood

This example demonstrates that the methods and compositions of the invention can be used to isolate nucleic acids from human blood, and that the extracted nucleic acids are stable at ambient temperature for at least several days.

In separate experiments, 4 mm punches of a piece of FTA paper (Whatman BioScience, Newton, Mass.) stained with human blood was put into a microcentrifuge tube containing 200 μl of either reagent LL-29 or reagent LL-30 (described in Example 1, above). Each tube was incubated for 10 minutes at either 100°, 65°, 55° C. or at ambient temperature, then briefly centrifuged in a microcentrifuge. 1 μl of each reaction was immediately used as the source of template DNA for an amplification reaction using the TAQ-MAN™ β-Actin Detection Kit (Applied Biosystems, Foster City, Calif,) and an ABI PRISM 7700™ Sequence Detection System (Applied Biosystems, Foster City, Calif.) according to the manufacturer's instructions and as described in Example 2, above.

Positive results were obtained for all samples tested, as indicated in the following chart. It also was noted that the threshold cycle for each sample generally decreased with increasing incubation temperature, indicating that the extraction efficiency is proportional to incubation temperature over the range tested.

To determine whether the extracted nucleic acids contain impurities that would cause them to degrade over time, each extraction was allowed to remain at ambient temperature for a period of three days, then used as the source of template DNA in amplification reactions as described above. Similar results were obtained, indicating that no significant degradation of the template DNA occurred since it was first extracted.

| Amplification Immediately Following Extraction | | | | | |
|---|---|---|---|---|---|
| Reagent | Incubation Temperature | Ct | Reagent | Incubation Temperature | Ct |
| LL-29 | RT | 34.2 | LL-30 | RT | 36.4 |
| LL-29 | 55° C. | 33.5 | LL-30 | 55° C. | 33.6 |
| LL-29 | 65° C. | 31.1 | LL-30 | 65° C. | 31.3 |
| LL-29 | 100° C. | 30.1 | LL-30 | 100° C. | 29.1 |

| Amplification After Three Days | | | | | |
|---|---|---|---|---|---|
| Reagent | Incubation Temperature | Ct | Reagent | Incubation Temperature | Ct |
| LL-29 | RT | 31.0 | LL-30 | RT | 31.9 |
| LL-29 | 55° C. | 31.2 | LL-30 | 55° C. | 31.1 |
| LL-29 | 65° C. | 29.2 | LL-30 | 65° C. | 30.5 |
| LL-29 | 100° C. | 26.9 | LL-30 | 100° C. | 27.1 |

RT = Room (ambient) temperature

EXAMPLE 9

Allelic Discrimination of DNA Extracted from Human Blood

This example demonstrates that the methods and compositions of the instant invention can be used to isolate nucleic acids from small amounts of human tissue.

For each tested blood sample, 25 μl of reagent LL-33 (described in Example 1, above) was added to 1.5 μl clot-free whole blood in a 1.5 ml microcentrifuge tube. Each tube was capped and a small hole made in the cap with a 24 gauge syringe needle. The tubes were incubated for 10 minutes in a boiling water bath, then allowed to cool for about 1.5 to 2 minutes. The cooled samples were then centrifuged at maximum speed in a tabletop microcentrifuge. 1 μl of the resulting supernatant was used in a standard TAQMAN™ (Applied Biosystems, Foster City, Calif.) PCR allelic discrimination assay optimized using guidelines found in the ABI PRISM 7700™ Sequence Detector (Applied Biosystems, Foster City, Calif.) user's manual. Thermocycling was performed using a GENEAMP™ PCR System 9700. After the PCR, the 96 well reaction plate was transferred to a ABI PRISM 7700™ (Applied Biosystems, Foster City, Calif.).

Figure 6A:
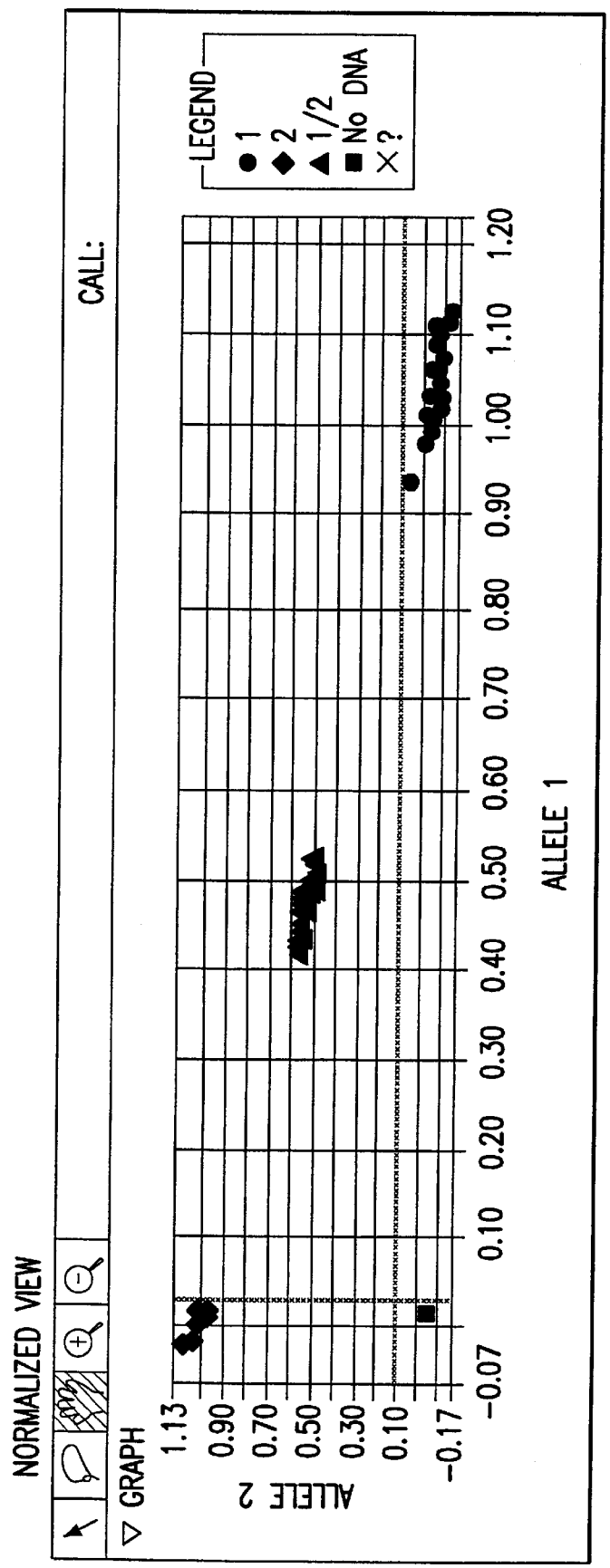
FIGS. 6A and 6B show normalized results (FIG. 6A) and dye view results (FIG. 6B) of an allelic discrimination of DNA extracted from human blood using the methods and compositions of the instant invention.
Figure 6B:
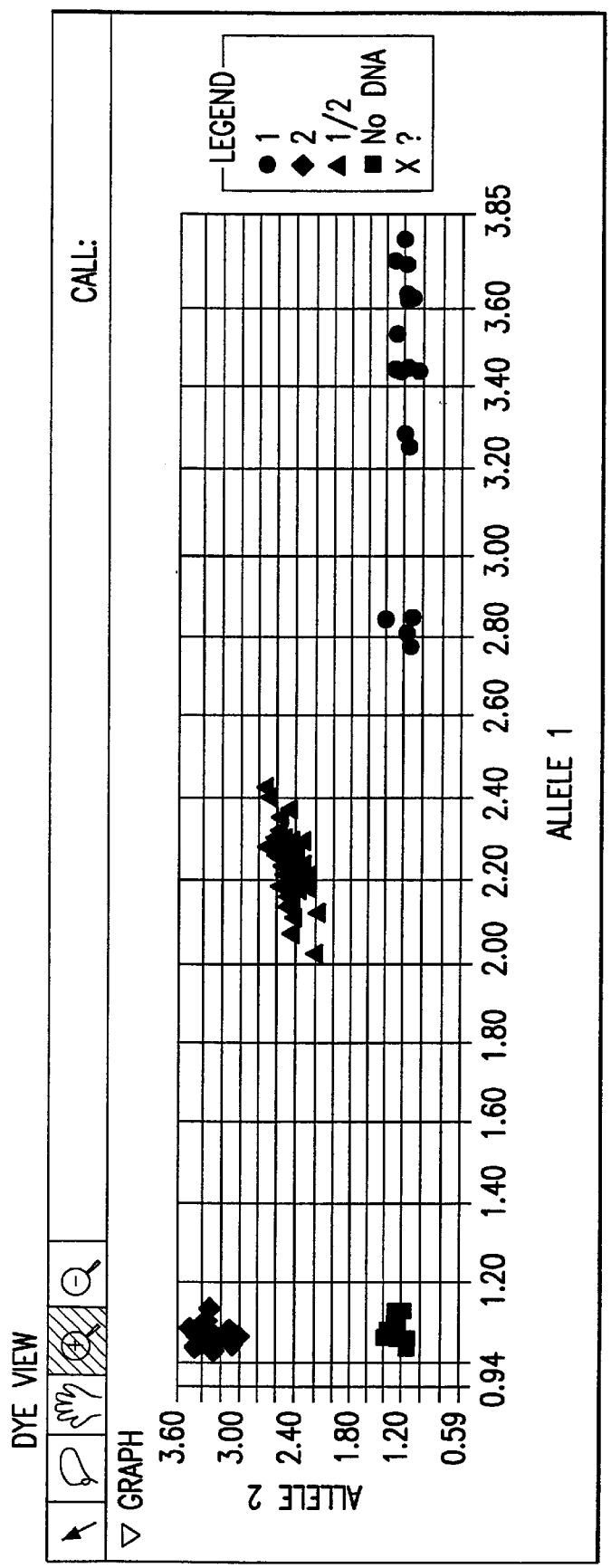

As shown in FIG. 6A, the allele groups show a tight clustering behavior in the normalized view. This also can be seen in the dye view (FIG. 6B). A slight spreading in the allele 1 group also was seen and is considered normal. Overall, the assay gave very reliable results.

EXAMPLE 10

Extraction and Amplification of DNA from Human Hair

This example demonstrates that the methods and compositions of the invention can be used to isolate nucleic acids from human hair.

0.2 M NaOH was added to human hair in a microfuge tube and incubated for 10 minutes in a boiling water bath. For the first two samples, 10 μl of the NaOH prep was added to 40 μl of reagent LL-33 (described in Example 1, above), then incubated for an additional 10 minutes in the boiling water bath. 1 μl was then used as the source of template DNA in a PCR reaction. For the second two samples, 10 μl of the NaOH prep was spotted on FTA paper (Whatman BioScience, Newton, Mass.). 4 mm punches were made and added to a microfuge tube containing 100 μl of LL-33. These tubes were then incubated in the boiling water bath for 10 minutes. 1 μl was then used as the source of template DNA in a PCR reaction. The PCR reaction products from all four reactions were then run on an agarose gel essentially as described above.

The first two reactions both produced a highly amplified product, indicating the abundant presence of template DNA and the absence of PCR inhibiting substances. The second two samples showed weaker and more variable amplification.

EXAMPLE 11

Extraction and Amplification of DNA from Feline Blood

This example demonstrates that the methods and compositions of the instant invention can be used to isolate nucleic acids from animal tissue.

Figure 7A:
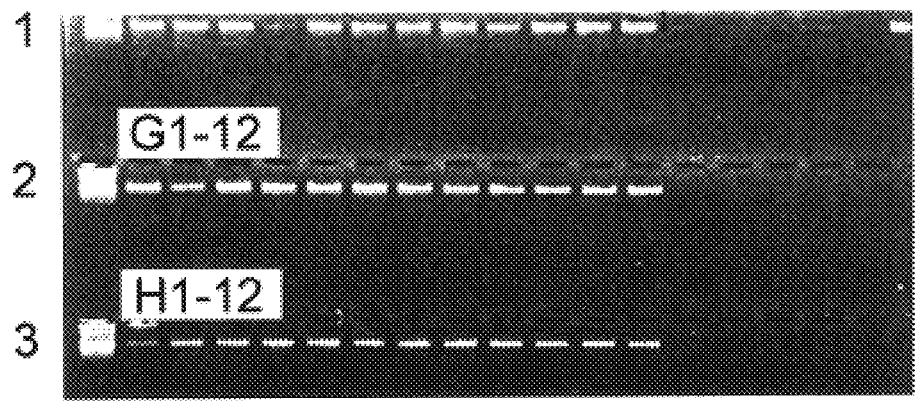
FIG. 7 shows electrophoretic separations on ethidium bromide-stained agarose gels of DNA extracted from feline blood using the methods and compositions of the instant invention and amplified by PCR.
Figure 7B:
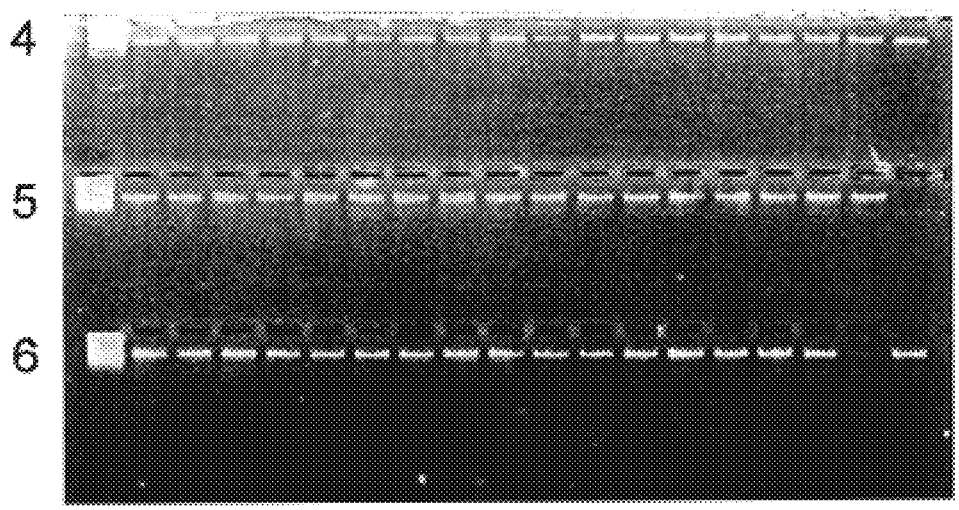

Blood drawn from a domestic cat was spotted onto FTA paper (Whatman BioScience, Newton, Mass.). 4 mm punches of the blood-stained paper were placed in 1 ml format tubes with 100 μl of reagent LL-33 (described in Example 1, above) and immersed in a boiling water bath for 10 minutes. 1 μl was used for PCR in a reaction volume of 50 μl. A portion of each PCR reaction were run on an agarose gel essentially as described in Example 5. As shown in FIG. 7A, rows 1, 2 and 3, lanes 2-13, and rows 4, 5 and 6, lanes 2-19 of FIG. 7B, virtually all 90 blood samples produced a band corresponding to the amplified target DNA sequence (lane 1 of each row is a molecular weight marker). It is estimated from these results that the amount of amplified nucleic acid in each sample would be sufficient to serve as template DNA in a subsequent DNA sequencing reaction.

EXAMPLE 12

Extraction and Amplification of DNA from a Pig's Tail

This example demonstrates that the methods and compositions of the instant invention can be used to isolate nucleic acids from an agricultural sample.

Cells from tails removed from postpartum piglets were smeared onto FTA paper (Whatman BioScience, Newton, Mass.). Nucleic acids were extracted from 4 mm punches essentially as described in Example 11, above. Primers were selected that specifically amplify a gene associated in swine with litter size. Each amplification reaction was run on an agarose gel and stained essentially as described in Example 5, above. Approximately 60 of the 90 samples tested gave detectable amplification products. The other 30 gave either no band at all or a "primer dimer" band that was slightly smaller than the desired amplicon band. The success rate was increased to 90 of 90 when the TAQMAN™ (Applied Biosystems, Foster City, Calif.) PCR system was used essentially as described in Example 2.

EXAMPLE 13

Extraction and Amplification of DNA from a Saline Mouthwash

This example demonstrates that the methods and compositions of the instant invention can be used to isolate nucleic acids from small amounts of human tissue.

In separate experiments, three human subjects rinsed their mouths with a saline mouthwash. 1 ml of each mouthwash recovered post-rinse was centrifuged for 1 minute. Each pellet was resuspended in 200gl of LL-33 (described in Example 1, above) and incubated for 10 minutes in a boiling water bath. For each extracted DNA sample, a series of 50 µl PCR reactions were set up containing 1, 3, 5, 7 and 10 µl of the extracted sample as the source of template DNA. Primers were selected to allow amplification of the Alu PV92 locus, which has allele sizes of 550 bp and 850bp. Each PCR reaction was run on an agarose gel and stained essentially as described in Example 5, above. Bands of the expected sizes were observed for every PCR reaction, indicating that PCR amplifiable DNA can be isolated the methods and compositions of the methods, even from trace amounts of human

EXAMPLE 14

Extraction and Amplification of DNA from Cultured Bacteria

This example demonstrates that the methods and compositions of the instant invention used to isolate nucleic acids from a wide range of prokaryotic organisms.

Each of the following 21 species of bacteria were grown as colonies on agar plates containing an appropriate growth medium:

| MCC # | Family | Genus | Species | Subspecies |
|---|---|---|---|---|
| 600 | Lactobacillaceae | Lactobacillus | *casei* | |
| 812 | Corynebacteriace | Coryne-bacterium | *variabile* | |
| 958 | Nocardiodaceae | Nocardia | *asteroides* | |
| 1852 | Xanthomonadace | Stenotrophomonas | *maltophilia* | |
| 2106 | Bacillaceae | Bacillus | *coagulans* | |
| 2107 | Staphylococcacea | Staphylococcus | *epidermidis* | |
| 2204 | Nocardioidaceae | Rhodococcus | *equi* | |
| 2263 | Streptococcaceae | Streptococcus | *agalactiae* | |
| 2633 | Pseudomonadac | Pseudomonas | *aeruginosa* | |
| 3322 | Moraxellaceae | Acinetobacter | *calcoaceticus* | |
| 3385 | Propionibacteriac | Propioinibacterium | *acnes* | |
| 3386 | Clostridiaceae | Clostridium | *difficile* | |
| 3420 | Fusobacteriaceae | Fusobacterium | *necrophorum* | necrophorum |
| 3485 | Enterobacteriace | Escherichia | *coli* | |
| 3555 | *B. Cereus* | Bacillus | *cereus* | |
| 3591 | Staphylococcacea | Staphylococcus | *aureus* | aureus |
| 3598 | Burkholderiaceae | Burkholderia | *cepacia* | |
| 3725 | Comamonadace | Delftia | *acidovorans* | |
| 4538 | Streptomycetacea | Streptomyces | *rimosus* | rimosus |
| 4557 | Gordaniaceae | Gordonia | *sputi* | |
| 4597 | Legionellaceae | Legionella | *anisa* | |

In separate experiments, ¼ to ½ loopful of cells from a single colony of each bacterium was suspended in 200 µl of LL-33 (described in Example 1, above) in a microcentrifuge tube. The suspension was mixed for 10 seconds or until the entire cell mass was suspended using a VORTEX™ laboratory mixer. Each suspension was incubated in a boiling water bath for 10 minutes, then centifuged at 16,000 g for 2 minutes.

PCR optimization was done on all strains using the PCR module of the MICROSEQ™ 500 16S rDNA Bacterial Sequencing Kit (Applied Biosystems, Foster City, Calif.). For each extraction, PCR reactions were performed using 2 µl, 1 µl, 0.1 µl and 0.02 µl of the extraction's supernatant fraction (the 0.1 µl and 0.02 µl volumes were obtained using serial dilutions of each extraction's supernatant fraction). Positive results, as determined using an agarose gel prepared essentially as described above, were obtained for every strain of bacterium for all four amounts of the supernatant fraction tested. The best results were obtained using 1 µl of the supernatant fraction.

PCR optimization was then done on all strains using the PCR module of the MICROSEQ™ Full Gene 16S rDNA Bacterial Sequencing Kit (Applied Biosystems, Foster City, Calif.), as described above, except that only 2 µl and 1 µl volumes of extraction supernatant fraction were used. Every amplification was successful except for strain 4557, which was not successfully amplified with either volume of extraction supernatant fraction (although faint bands were visible on the gel). For the remaining strains, 1 µl of the extraction supernatant fraction gave better results than 2 µl.

EXAMPLE 15

Effect of Incubation Temperature on Extraction Efficiency

This example demonstrates that a wide range of incubation temperatures can be used to practice the instant invention.

In separate experiments, egg and ground beef enrichments were prepared as described in Example 3, above. 0.9 ml aliquots of each enrichment were added to 0.1 ml of an appropriately diluted overnight culture of *E. coli* to give a concentration of bacteria in the amplification reactions described below of 335cfu/reaction. Each 1 ml post-spiked enrichment culture was centrifuged to pellet the cells and the supernatant fraction was discarded. The cell pellets were resuspended in 200 µl of reagent LL-33 (described in Example 1, above). Each resuspended cell pellet was incubated at 21°, 37°, 60°, 70°, 80°, 90° or 100° C. After centrifugation, the lysates were analyzed using the TAQ-MAN™ *E. coli* O157:H7 Detection Assay Kit (Applied Biosciences, Foster City, Calif.) and the ABI PRISM 7700™ (Applied Biosystems, Foster City, Calif.), essentially as described in Example 3.

Figure 8A:
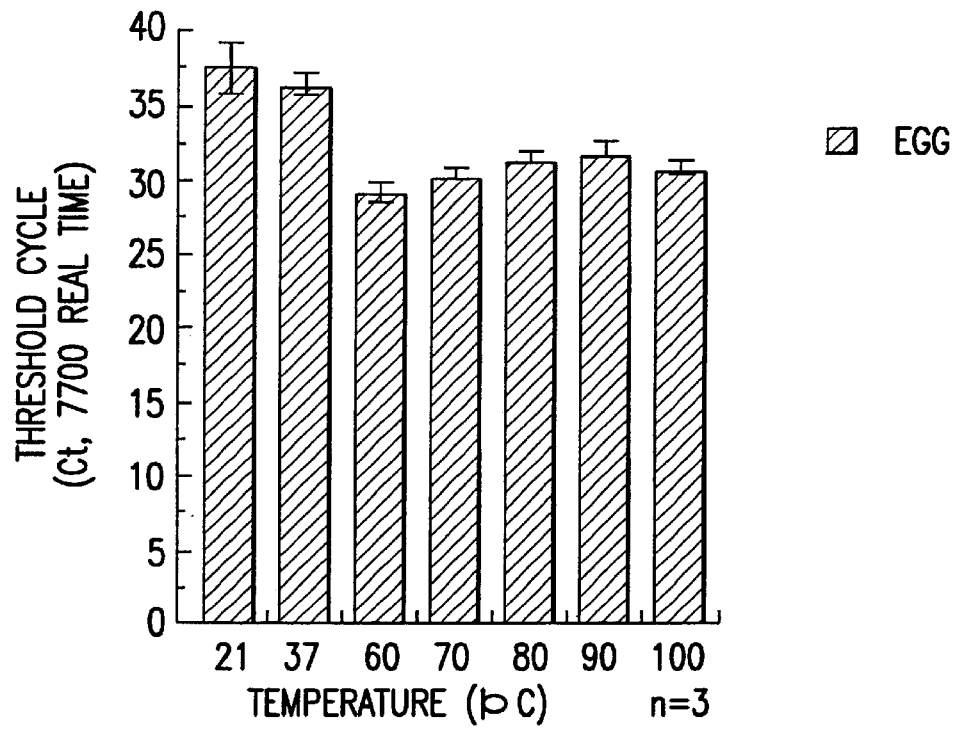
FIG. 8 shows the effects of incubation temperature on extraction efficiency using the methods and compositions of the instant invention as measured by the threshold cycle of PCR reactions.
Figure 8B:
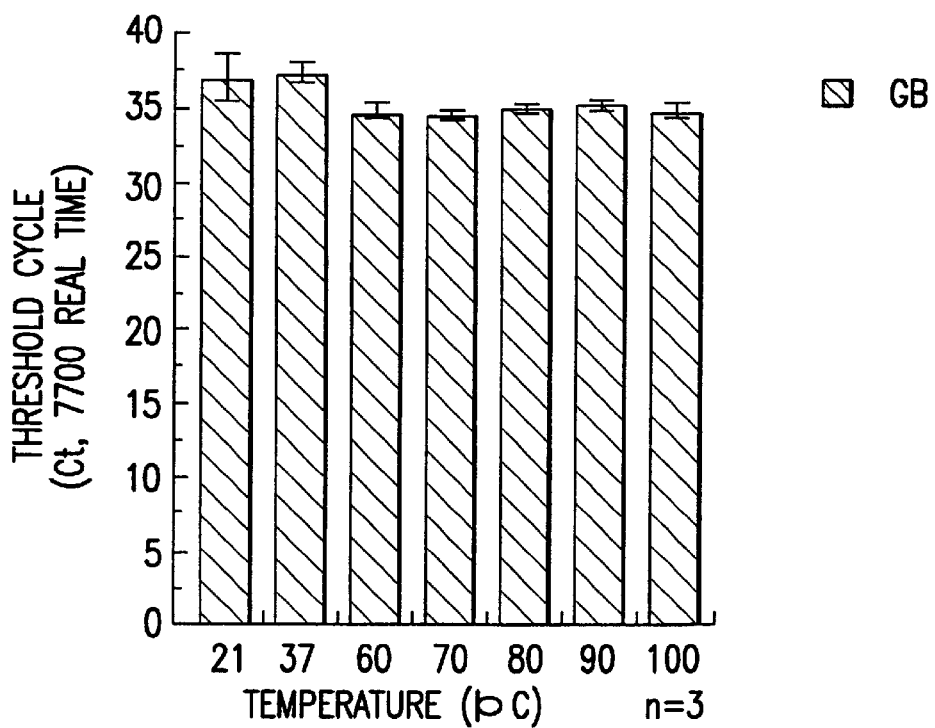

As shown in FIG. 8, every amplification was successful (i.e., every amplification had a threshold cycle of less than 40). However, it was noted that the lower temperatures tested (21° and 37° C.) demonstrated an extraction efficiency lower than that achieved using the higher incubation temperatures.

What is claimed is:

1. A method of preparing a nucleic acid for subsequent manipulation, comprising contacting a sample suspected of containing the nucleic acid with an aqueous nucleic acid extraction reagent, wherein the nucleic acid extraction reagent comprises about 0.1 wt % to about 18 wt % sodium metasilicate and about 0.05 wt % to 80 wt % of a water soluble substituted ether having a total of from 2 to 12 carbon atoms and has a pH in the range of about pH 7 to about pH 10.

2. A method of isolating a nucleic acid from a sample, comprising the steps of:

contacting a sample suspected of containing a nucleic acid with an aqueous nucleic acid extraction reagent; and recovering the nucleic acid, wherein the nucleic acid extraction reagent comprises about 0.1 wt % to about 18 wt % sodium metasilicate and about 0.05 wt % to 80 wt % of a water soluble substituted ether having a total of from 2 to 12 carbon atoms and has a pH in the range of about pH 7 to about pH 10.

3. The method of claim 2, in which the sample comprises a cell or virus and the sample is contacted with the aqueous nucleic acid extraction reagent for a period of time sufficient to lyse the cell or virus.

4. The method of claim 1 or 2, in which the water soluble substituted ether is an alkoxy alkyl alcohol, an aryloxy alkyl alcohol or an alkoxy aryl alcohol.

5. The method of claim 4, in which the water-soluble substituted ether has the formula $CH_3(CH_2)_m-O-(CH_2)_n CH_2-OH$, where m and n are, independently of one another, integers between 0 and 6.

6. The method of claim 1 or 2, in which the substituted ether is selected from the group consisting of 2-butoxyethanol, 2-methoxyethanol, 2-phenoxyethanol, diethylene glycol monoethyl ether, diethylene glycol monobutyl ether, diethylene glycol dibutyl ether, 2-butoxyethanol, diethylene glycol-monopentyl ether, diethylene glycol-diethyl ether, ethylene glycol-monomethyl ether, ethylene glycol-monoethyl ether, ethylene glycol-monobutyl ether, ethylene glycol-dimethyl ether and ethylene glycol-diethyl ether.

7. The method of claim 1 or 2, in which the ratio of sodium metasilicate to substituted ether is about 1:1.1 to about 1:1.5.

8. The method of claim 7, in which the ratio is 1:1.3.

9. The method of claim 1 or 2, in which the pH of the extraction reagent is between about pH 8 to pH 9.

10. The method of claim 1 or 2, in which the contacting step is carried out at a temperature in the range of about 25° C. to about 120° C.

11. The method of claim 1 or 2, in which the contacting step is carried out for a period of about 5 minutes to about 30 minutes.

12. The method of claim 1 or 2, in which the sample is a food sample.

13. The method of claim 1 or 2, in which the sample is a clinical sample.

14. The method of claim 1 or 2, in which the sample is a forensic sample.

15. The method of claim 1 or 2, in which the sample is an agricultural sample.

16. The method of claim 1 or 2, in which the sample is an environmental sample.

17. The method of claim 1 or 2, in which the sample is a microorganism grown in culture.

18. An aqueous nucleic extraction reagent, comprising:

greater than 0.8 wt % to less than 5 wt % sodium metasilicate;

greater than 1 wt % to less than 5 wt % of a water-soluble substituted ether, and which has a pH in the range of about pH 7 to pH 10.

19. The nucleic acid extraction reagent of claim 18, wherein the ether is selected from the group consisting of an alkoxy alkyl alcohol, an aryloxy alkyl alcohol and an alkyloxy aryl alcohol.

20. The nucleic acid extraction reagent of claim 18, wherein the ether is selected from the group consisting of 2-butoxyethanol, 2-methoxyethanol, 2-phenoxyethanol, diethylene glycol monoethyl ether, diethylene glycol monobutyl ether, diethylene glycol dibutyl ether, 2-butoxyethanol, diethylene glycol-monopentyl ether, diethylene glycol-diethyl ether, ethylene glycol-monomethyl ether, ethylene glycol-monoethyl ether, ethylene glycol-monobutyl ether, ethylene glycol-dimethyl ether and ethylene glycol-diethyl ether.

21. The nucleic acid extraction reagent of claim 18, further comprising citric acid.

22. The nucleic acid extraction reagent of claim 18, further comprising a buffer.

23. The nucleic acid extraction reagent of claim 18, further comprising a chelator.

24. The nucleic acid extraction reagent of claim 18, further comprising a preservative.

25. The nucleic acid extraction reagent of claim 18, further comprising a stabilizer.

26. The nucleic acid extraction reagent of claim 18, wherein the ratio of the weight percent sodium metasilicate to the weight percent ether is about 1:1.3.

27. A kit, comprising a nucleic acid extraction reagent and a PCR primer, wherein the nucleic acid extraction reagent comprises about 0.1 wt % to about 18 wt % sodium metasilicate and about 0.05 wt % to 80 wt % of a water soluble substituted ether having a total of from 2 to 12 carbon atoms and has a pH in the range of about pH 7 to about pH 10.

* * * * *

UNITED STATES PATENT AND TRADEMARK OFFICE
CERTIFICATE OF CORRECTION

PATENT NO.     : 6,503,716 B1
DATED          : October 7, 2003
INVENTOR(S)    : Lucy Tung-Yi Lai and Michael Shiu-Yan Ho It is certified that error appears in the above-identified patent and that said Letters Patent is hereby corrected as shown below:

<u>Column 1,</u>
Line 4, after the title of the invention add -- The U.S. Government has a paid-up license in this invention and the right in limited circumstances to require the patent owner to license on reasonable terms as provided for by the terms of Award No. 70NANB8H4002 awarded by the National Institute of Standards and Technology (NIST) to the Perkin-Elmer Corp., Applied Biosystems Division. --

Signed and Sealed this

Eighteenth Day of November, 2003

JAMES E. ROGAN
*Director of the United States Patent and Trademark Office*